United States Patent
Ong et al.

(10) Patent No.: US 9,335,195 B2
(45) Date of Patent: May 10, 2016

(54) MULTIPHASE METER TO PROVIDE DATA FOR PRODUCTION MANAGEMENT

(75) Inventors: Joo Tim Ong, Houston, TX (US); Songhua Chen, Katy, TX (US); Terry R. Bussear, Spring, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 333 days.

(21) Appl. No.: 13/028,553

(22) Filed: Feb. 16, 2011

(65) Prior Publication Data

US 2012/0209541 A1 Aug. 16, 2012

(51) Int. Cl.
| | |
|---|---|
| G01F 1/00 | (2006.01) |
| G01F 1/74 | (2006.01) |
| G01F 1/56 | (2006.01) |
| G01F 1/58 | (2006.01) |
| G01F 1/60 | (2006.01) |
| G01N 24/08 | (2006.01) |
| G01R 33/383 | (2006.01) |
| G01V 3/32 | (2006.01) |

(52) U.S. Cl.
CPC .. G01F 1/74 (2013.01); G01F 1/56 (2013.01); G01F 1/586 (2013.01); G01F 1/588 (2013.01); G01F 1/60 (2013.01); G01N 24/081 (2013.01); G01N 24/082 (2013.01); G01R 33/383 (2013.01); G01V 3/32 (2013.01)

(58) Field of Classification Search
CPC ........................................ G06F 19/00
USPC ........................................ 702/45
See application file for complete search history.

(56) References Cited

U.S. PATENT DOCUMENTS

| | | | |
|---|---|---|---|
| 3,854,038 A * | 12/1974 | McKinley | 702/46 |
| 5,331,450 A | 7/1994 | Heep et al. | |
| 5,855,243 A * | 1/1999 | Bragg | 166/275 |
| 5,987,385 A * | 11/1999 | Varsamis et al. | 702/6 |
| 6,076,049 A | 6/2000 | Lievois et al. | |
| 6,292,756 B1 * | 9/2001 | Lievois et al. | 702/50 |
| 6,331,775 B1 | 12/2001 | Thern et al. | |
| 6,349,766 B1 * | 2/2002 | Bussear et al. | 166/113 |
| 6,737,864 B2 | 5/2004 | Prammer et al. | |
| 6,859,034 B2 * | 2/2005 | Chen | 324/303 |
| 7,253,618 B1 * | 8/2007 | Freedman et al. | 324/303 |

(Continued)

FOREIGN PATENT DOCUMENTS

WO WO2008013789 A2 1/2008

OTHER PUBLICATIONS

F.E. Londono, et al (Simplified Correlations for Hydrocarbon Gas Viscosity and Gas Density—Validation and Correlation of Behavior Using a Large-Scale Database, 2002.*

(Continued)

*Primary Examiner* — Aditya Bhat
(74) *Attorney, Agent, or Firm* — Cantor Colburn LLP

(57) ABSTRACT

A method and apparatus for determining a volume of a phase of a multiphase fluid flowing in a production tubular is provided. A magnetic field is imparted on the fluid to align nuclei of the multiphase fluid along a direction of the magnetic field. A radio frequency signal is transmitted into the multiphase fluid to excite the nuclei, and a signal is detected from the nuclei responsive to the transmitted radio frequency signal. An amplitude of the detected signal is determined and the volume of the phase flowing in the production tubular is determined using the determined amplitude and an amplitude of a calibration signal.

13 Claims, 18 Drawing Sheets

(56) References Cited

U.S. PATENT DOCUMENTS

| | | | |
|---|---|---|---|
| 7,501,819 B2* | 3/2009 | Ong | 324/306 |
| 7,872,474 B2* | 1/2011 | Pusiol et al. | 324/306 |
| 8,043,648 B2* | 10/2011 | Edelman et al. | 426/602 |
| 8,212,557 B2* | 7/2012 | Pusiol et al. | 324/306 |
| 8,729,893 B2* | 5/2014 | Li et al. | 324/303 |
| 2002/0140425 A1* | 10/2002 | Prammer et al. | 324/303 |
| 2002/0153888 A1* | 10/2002 | Kruspe et al. | 324/303 |
| 2002/0175682 A1* | 11/2002 | Chen et al. | 324/303 |
| 2003/0001569 A1* | 1/2003 | Chen et al. | 324/303 |
| 2004/0222791 A1* | 11/2004 | Chen | 324/303 |
| 2006/0071661 A1* | 4/2006 | Ong | 324/303 |
| 2006/0255799 A1 | 11/2006 | Reiderman | |
| 2007/0114996 A1* | 5/2007 | Edwards | 324/303 |
| 2007/0196497 A1* | 8/2007 | Pouliquen et al. | 424/489 |
| 2007/0222444 A1 | 9/2007 | Reiderman | |
| 2008/0154509 A1* | 6/2008 | Heaton | 702/7 |
| 2008/0174309 A1* | 7/2008 | Pusiol et al. | 324/306 |
| 2009/0032303 A1* | 2/2009 | Johnson | 175/40 |
| 2009/0157315 A1* | 6/2009 | Ong | 702/6 |
| 2009/0248311 A1* | 10/2009 | Coope et al. | 702/13 |
| 2009/0255669 A1* | 10/2009 | Ayan et al. | 166/250.15 |
| 2009/0293634 A1* | 12/2009 | Ong | 73/861.04 |
| 2009/0294123 A1* | 12/2009 | Mescall et al. | 166/250.01 |
| 2010/0264916 A1 | 10/2010 | Pusiol | |
| 2011/0025324 A1* | 2/2011 | Fransson et al. | 324/307 |
| 2011/0109308 A1* | 5/2011 | Pusiol et al. | 324/306 |
| 2011/0153216 A1* | 6/2011 | Coope et al. | 702/8 |
| 2011/0181278 A1* | 7/2011 | Chen et al. | 324/303 |
| 2012/0092006 A1* | 4/2012 | Li et al. | 324/306 |
| 2012/0209541 A1* | 8/2012 | Ong et al. | 702/45 |
| 2012/0310553 A1* | 12/2012 | Ong | 702/49 |
| 2013/0018602 A1* | 1/2013 | Ong et al. | 702/45 |

OTHER PUBLICATIONS

Kokal, et al, Reducing Pressure Drop in Offshore Pipelines by Controlling the Viscosities of Pressurized Emulsions, 2003.*

International Search Report and Written Opinion dated Aug. 31, 2012 for International Application No. PCT/US2012/021716.

Kokal, Sunil, et al., "Reducing Pressure Drop in Offshore Pipelines by Controlling the Viscosities of Pressurized Emulsions," SPE 81511, SPE Middle East Oil Show, Bahrain, Apr. 5-8, 2003, pp. 1-10.

Londono, F.E. et al., "Simplified Correlations for Hydrocarbon Gas Viscosity and Gas Density—Validation and Correlation of Behavior Using a Large-Scale Database," SPE 75721, SPE Gas Technology Symposium, Calgary, Alberta, Canada, Apr. 30-May 2, 2002, pp. 1-16.

* cited by examiner

MULTIPHASE METER TO PROVIDE DATA FOR PRODUCTION MANAGEMENT

BACKGROUND OF THE DISCLOSURE

1. Field of the Disclosure

The present disclosure relates generally to a measurement apparatus and methods for estimating downhole fluid characteristics.

2. Description of the Related Art

In the oil and gas industry it has become increasingly important in recent years to obtain measurements of the flow rate and phase ratio of multiphase fluids such as those produced by drilling operations and the compositions of the downhole fluid.

In order to measure the flow rate and ratio properties of such multiphase fluids accurately enough to satisfy the operator's requirements it is currently known to use techniques such as Nuclear Magnetic Measurement (NMR) and Electronic Spin Resonance (ESR) analysis. However, currently available systems for measuring such properties using these techniques require a number of separate components which employ a variety of operational and analytical techniques and often involve a number of discrete devices each adapted to measure a particular property of the fluid flow. For example a device for detecting the fraction of one phase may be supplied along with a device for detecting the fraction of another phase and another device to measure the overall flow rate. Also, such techniques are generally not utilized for compositional analysis of hydrocarbons in downhole fluids.

SUMMARY OF THE DISCLOSURE

In one aspect, the present disclosure provides a method of determining a volume of a phase of a multiphase fluid flowing in a tubular, including: imparting a magnetic field on the fluid to align nuclei of the multiphase fluid along a direction of the magnetic field; transmitting a radio frequency signal into the multiphase fluid to excite the nuclei; detecting a signal from the nuclei responsive to the transmitted radio frequency signal; determining an amplitude of the detected signal; and determining the volume of the phase flowing in the tubular using the determined amplitude and an amplitude of a calibration signal.

In another aspect, the present disclosure provides an apparatus for determining a volume of a phase of a multiphase fluid flowing in a tubular, the apparatus including a source configured to impart a primary magnetic field on the fluid to align nuclei of the multiphase fluid along a direction of the primary magnetic field; a source configured to transmit a radio frequency signal into the multiphase fluid to excite the nuclei; a detector for detecting a signal from the nuclei responsive to the transmitted radio frequency signal; and a processor configured to determine an amplitude of the detected signal and the volume of the phase flowing in the tubular using the determined amplitude of the detected signals and an amplitude of a calibration signal.

In yet another aspect, the present disclosure provides a method of determining stability of an emulsion flowing in a production string, the method including imparting a primary magnetic field on the emulsion to align nuclei of the emulsion along a direction of the primary magnetic field; transmitting a radio frequency signal into the emulsion flowing in the production string; detecting a signal from the nuclei of the emulsion responsive to the transmitted radio frequency signal; determining an amplitude of the detected signal; determining a water cut of the emulsion using the obtained amplitude; determining a relaxation rate of a signal obtain from nuclei of the emulsion excited in response to the transmitted radio frequency signal; obtaining a viscosity of the emulsion from the determined relaxation time; and determining the stability of the emulsion from the determined emulsion viscosity and the water cut of the emulsion.

Examples of the more important features of the methods and apparatus for analyzing the composition of a hydrocarbon have been summarized rather broadly in order that the detailed description thereof that follows may be better understood and in order that the contributions they represent to the art may be appreciated. There are, of course, additional features of the methods and apparatus that are described hereinafter and which will form the subject of any claims that may be made pursuant to this disclosure.

BRIEF DESCRIPTION OF THE DRAWINGS

For detailed understanding of the apparatus and methods for compositional analysis of hydrocarbons in a downhole fluid, reference should be made to the following detailed description, taken in conjunction with the accompanying drawing, in which like elements are generally designated by like numerals, and in which.

DETAILED DESCRIPTION OF THE DISCLOSURE

Figure 1:
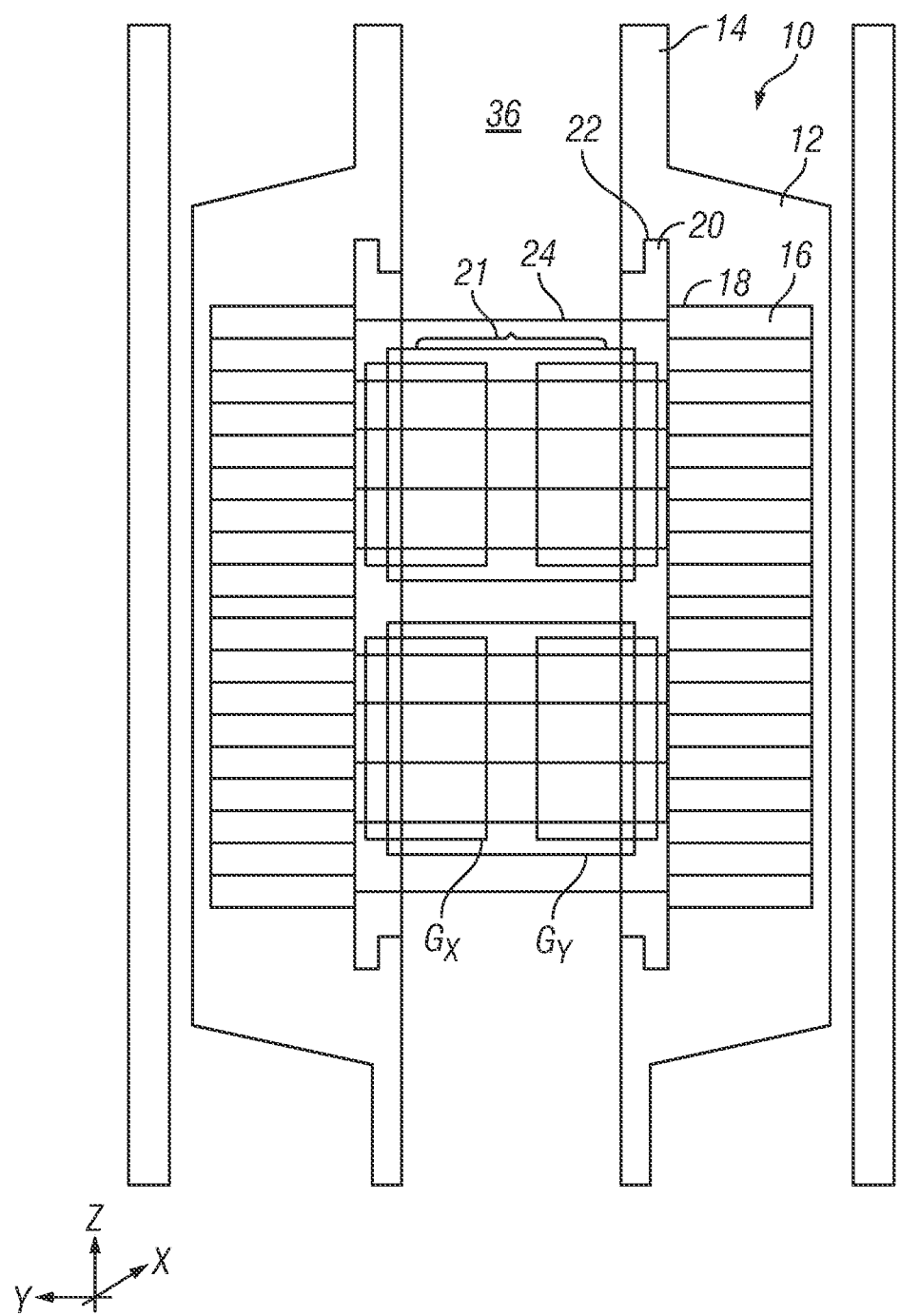
FIG. 1 is a transverse side view of one embodiment of the apparatus according to the present disclosure.
Figure 1A:
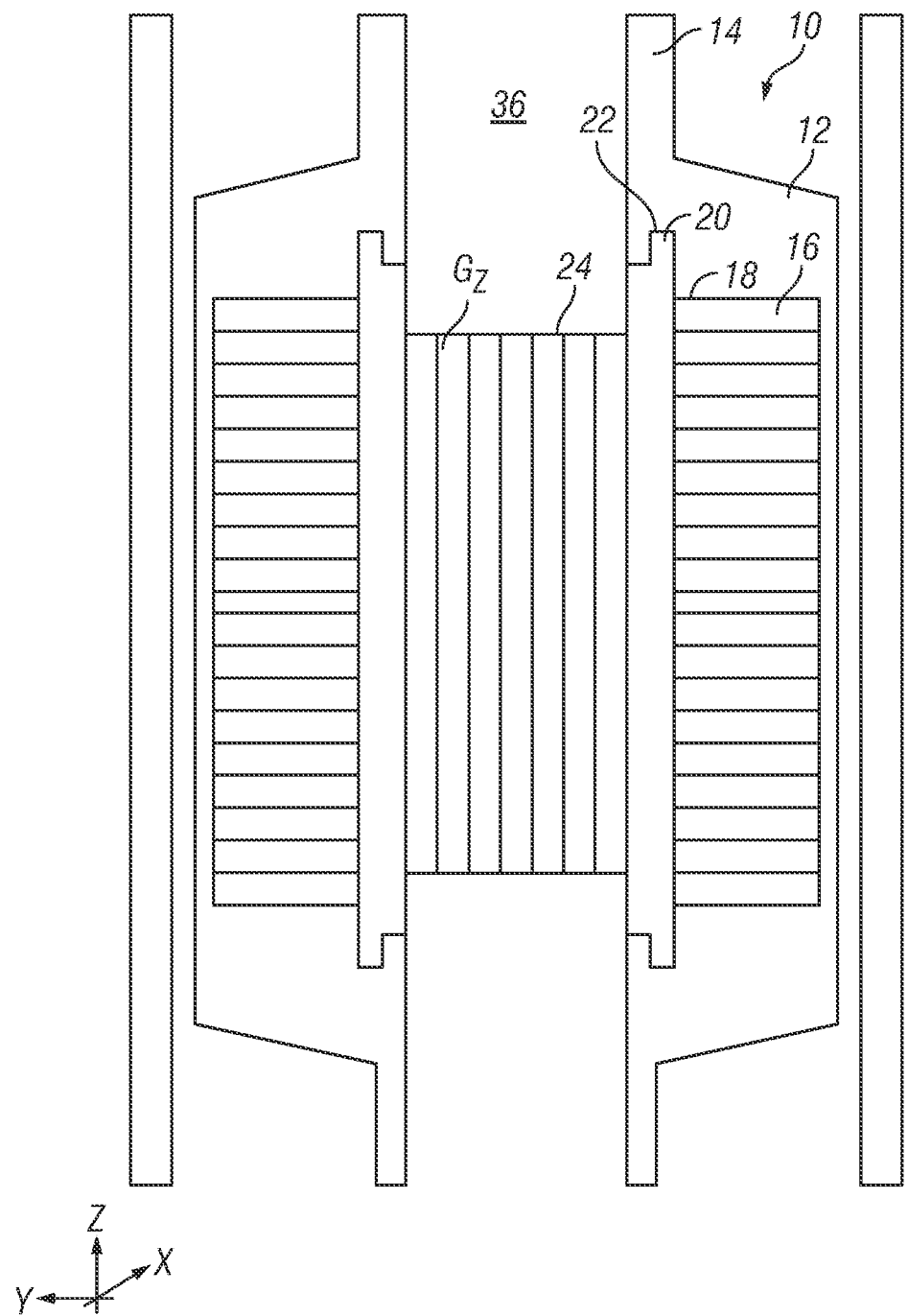
FIG. 1a is a transverse side view of the apparatus of FIG. 1 showing magnetic gradient coils which act in the direction of the z-axis with respect to the reference axes indicated on FIG. 1.
Figure 2:
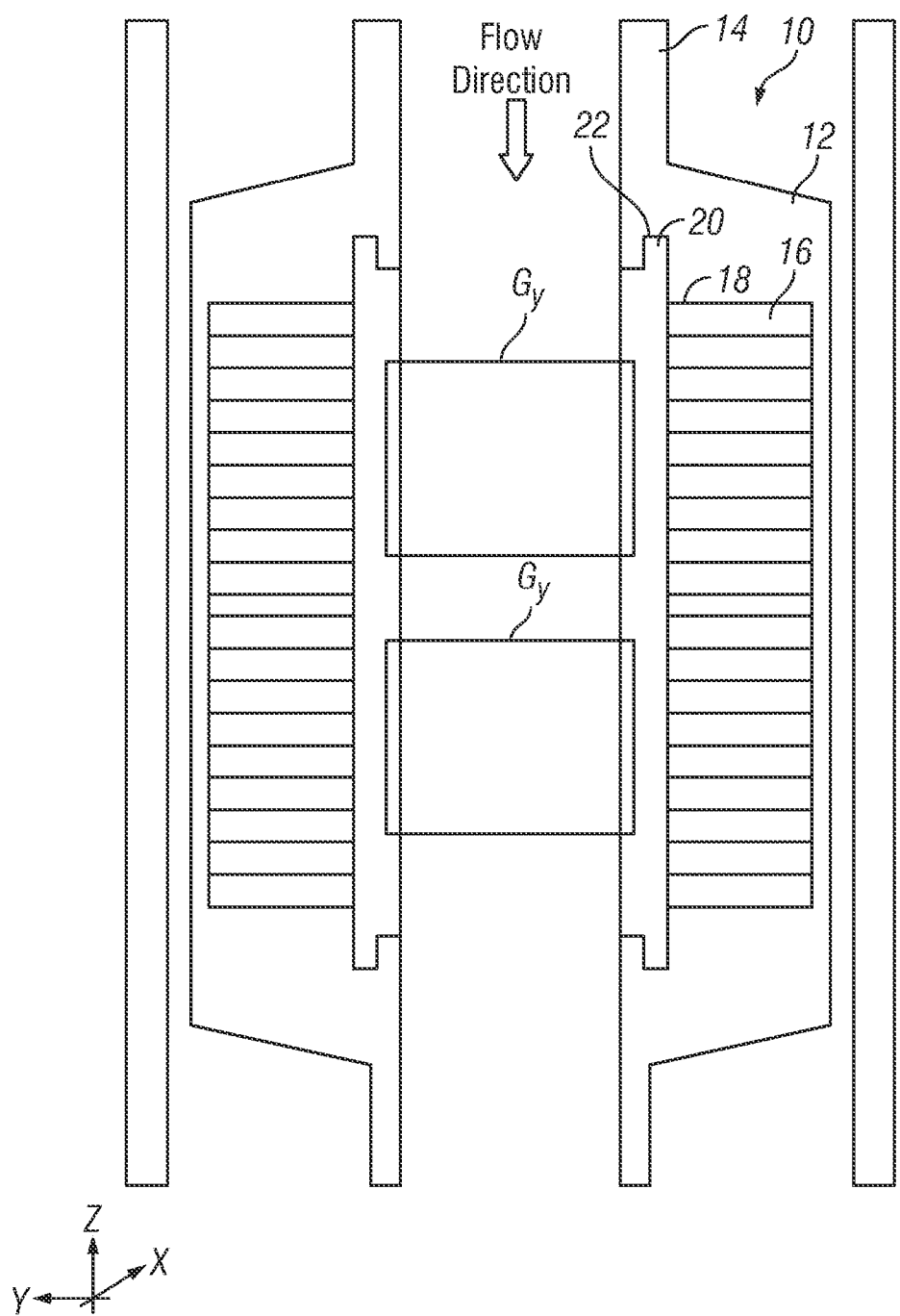
FIG. 2 is a transverse side view of the apparatus of FIG. 1 showing magnetic gradient coils which act in the direction of the y-axis with respect to the reference axes indicated on FIG. 1.
Figure 3:
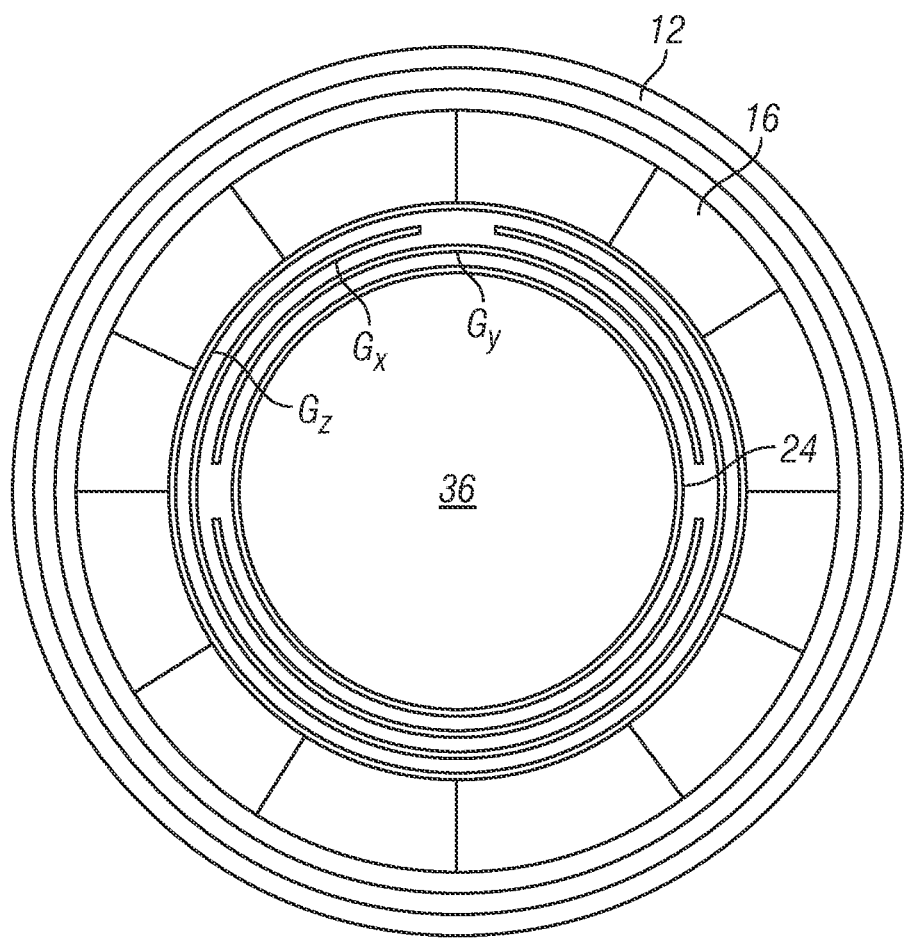
FIG. 3 is a cross sectional view of the apparatus of FIG. 1 showing the components of the magnetic gradient coils which act in the x, y and z directions with respect to the reference axes indicated on FIG. 1.
Figure 4:
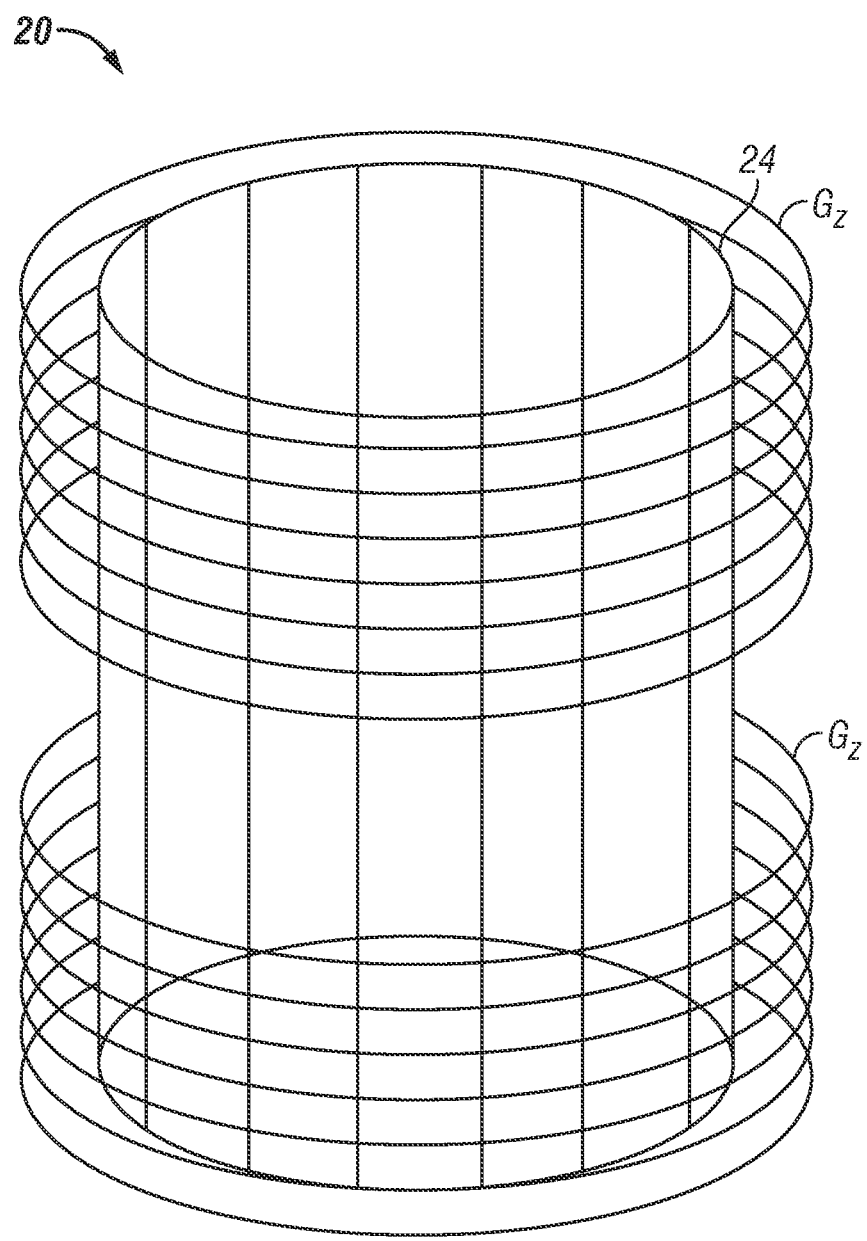
FIG. 4 is a schematic view of the component of the gradient coils which act in the z-axis direction with respect to the reference axes of FIG. 1, arranged around combined transmission and reception coils in accordance with a particular embodiment of the disclosure.
Figure 5:
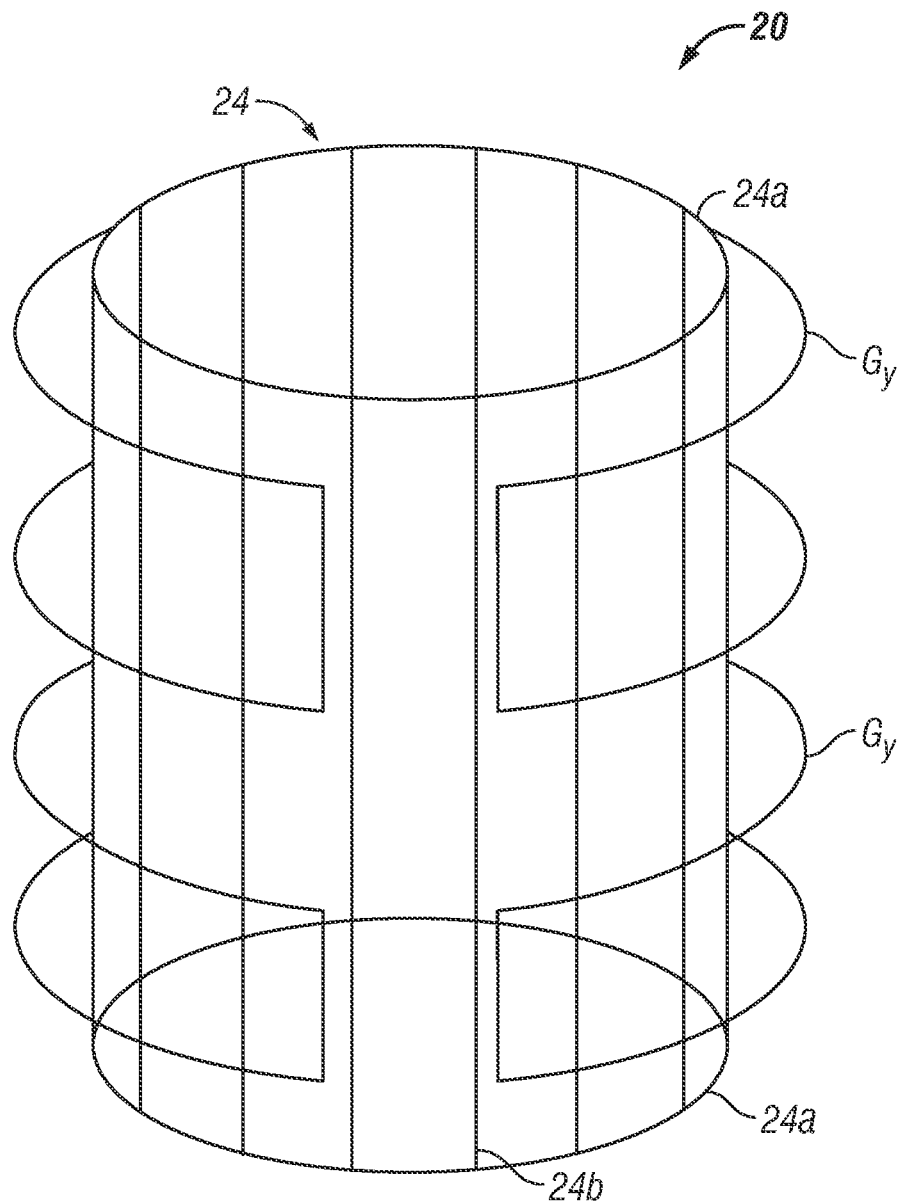
FIG. 5 is a schematic view of the gradient coils which act in the y-axis direction with respect to the reference axes of FIG. 1, arranged around combined transmission and reception coils in accordance with one embodiment of the present disclosure.

Referring to FIG. 1 the apparatus 10 in accordance with the first embodiment of the present invention comprises an outer housing 12 which surrounds a section of a fluid flow pipe 14, such as production tubing, by locking thereto via a suitable locking mechanism. Inside the housing 12 is located a primary permanent magnet 16 in an outermost recess 18 and a secondary electromagnet housing 20 located in an innermost recess 22. The electromagnet housing 20 has located within it an electromagnet 21 which comprises electromagnet coils Gx, Gy and (as shown in FIG. 1a) Gz. Combined transmission and reception coils 24 are also provided within the inner diameter of the electromagnet housing 20.

Outer housing 12 provides magnetic shielding which substantially minimizes leakage of magnetic field outside the apparatus 10, and provides safe handling of the tool. This also improves the signal transmission and reception performance of the coils 24 by minimizing interference from surrounding radio signals such as FM radio signals. Housing 12, in the present embodiment, comprises low permeability iron, (typically µr<1.00) which provides the main outer body of the apparatus. The material is typically around 10 mm thick around the mid portion of the apparatus 10 and thicker toward the ends of the apparatus 10, typically up to a thickness of around 60 mm. The skilled reader will realize that different thickness and material may be used in the housing 12 in order to suit the particular application.

Figure 6:
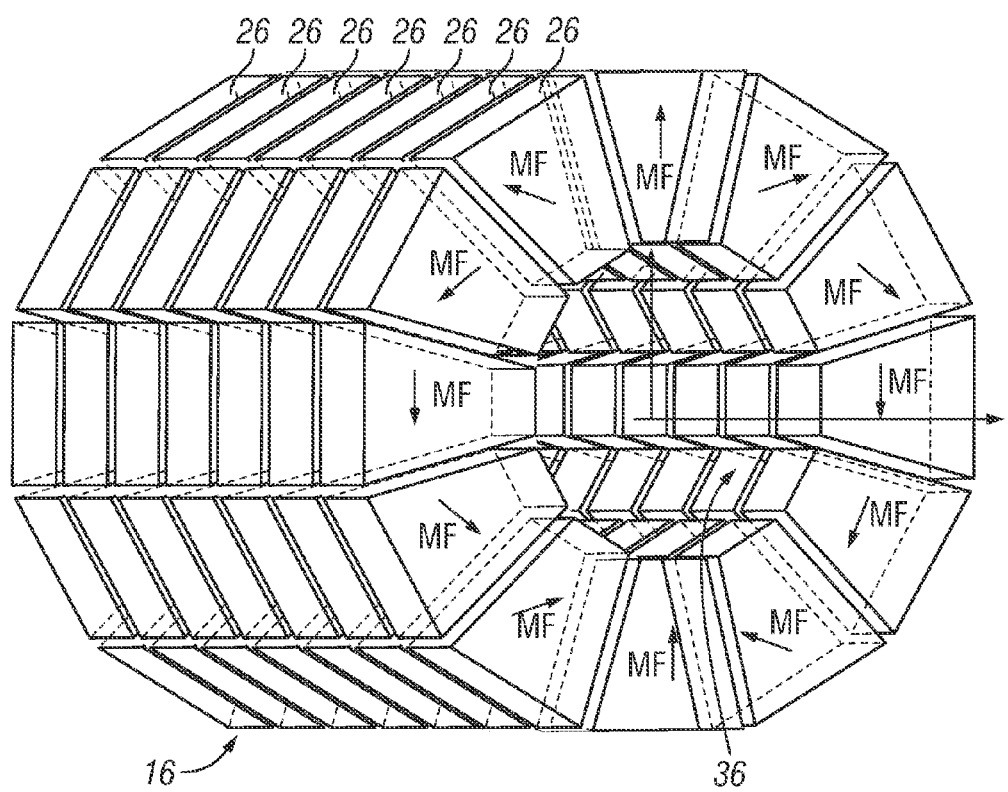
FIG. 6 is an illustration of a magnetic field orientation in order to produce the homogeneous magnet used in accordance with the present disclosure.
Figure 8:
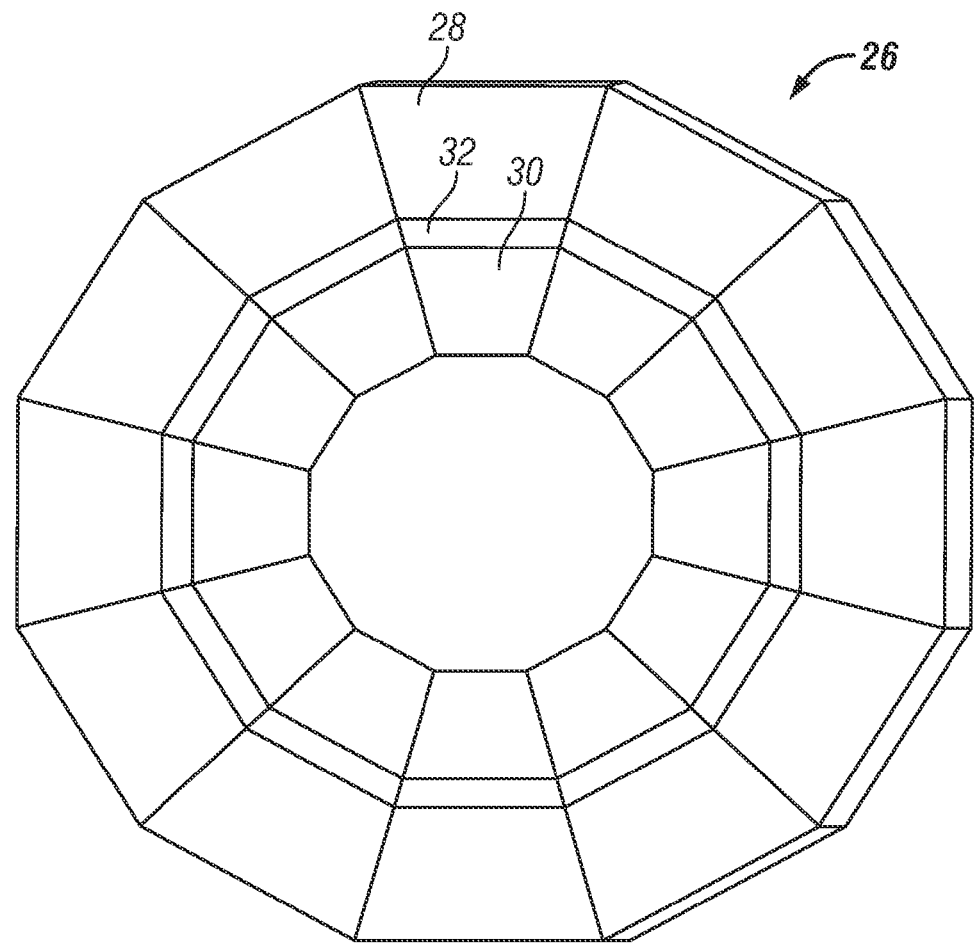
FIG. 8 is a schematic cross sectional diagram of the primary magnet composition used in accordance with the present disclosure.
Figure 9:
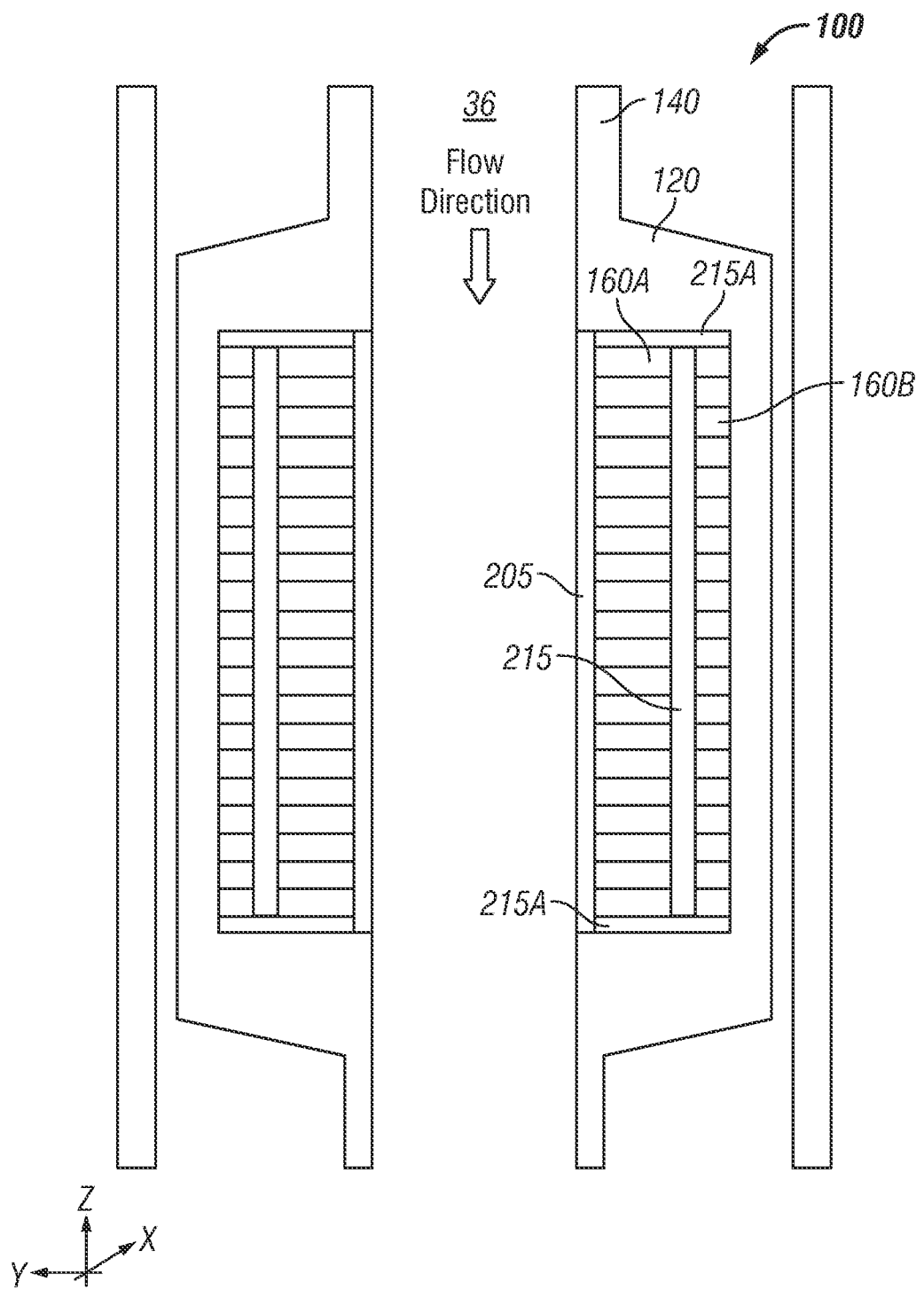
FIG. 9 is a transverse side view of another embodiment of the apparatus according to the present invention without the gradient and transmission coils shown.

Referring particularly to FIGS. 6 and 8, the primary permanent magnet 16 comprises a number of concentrically arranged magnetic cells 26 which are stacked together. Each magnetic cell 26 comprises a number of outer segments 28 (FIG. 8) arranged adjacent a number of inner segments 30 such that a circumferential band of inner segments 30 are arranged within a circumferential band of outer segments 28. Flat plates 32 are positioned between the circumferential band of outer segments 28 and the circumferential band of inner segments 30 such that a circumferential band of plates 32 is located between the outer segments 28 and the inner segments 30. The plates 32 are typically formed of an iron based material having a permeability of greater than 1000.

Aperture 34 is provided in the centre of each cell 26 to allow the flow of fluid therethrough as will be discussed subsequently. When the cells 28 are stacked together they form a throughbore 36 (as shown in FIG. 6) along the length of the magnet 16. The iron plates 32 ensure that the resultant magnetic field produced by inner segments 30 and outer segments 28 is focused toward the center of the aperture 34 of each cell and hence along the throughbore 36 of the apparatus 10.

The skilled reader will understand that the term permanent magnet in this context is taken to mean a magnet which provides a constant magnetic field without requiring, for example, an electric current in order to create the magnetic field. In an alternative embodiment, the permanent magnet may be an electromagnet which provides a continuous and substantially homogeneous magnetic field.

The direction of the magnetic field vectors (indicated by MF in FIG. 6) of each outer 28 and inner 30 segment is carefully arranged during manufacture in order to create a resultant magnetic field for the magnet 16 which is as close to being homogeneous as possible throughout the throughbore of the magnet 16. This ensures that the magnetic field present within the throughbore 36 of the magnet 16 remains consistent within the throughbore 36 irrespective of the location within the throughbore 36 that the magnetic field is experienced. Typically, the required homogeneity is in the region of around 1.0 ppm. This ensures accurate measurements are possible using the apparatus 10 in conjunction with the NMR techniques as will be discussed subsequently.

The secondary electromagnet housing 20 is provided with a combined transmission and reception coil 24 which is capable of both transmitting a radio frequency pulse and detecting the radio frequency emitted by nuclei excited by such a radio frequency pulse. In the embodiment shown in the Figures, the coil 24 comprises a pair of circular loops 24a at the top and bottom of the coil 24 connected by circumferentially spaced connecting coils 24b to form a "birdcage" configuration. This provides the apparatus 10 with the ability to both transmit a radio frequency pulse evenly throughout the throughbore 36 and competently detect radio frequency signals emitted by nuclei at any location within the throughbore 36 of the apparatus 10. Rather than a "birdcage" configuration the coils may alternatively be arranged to provide a "saddle coil" configuration depending upon the application.

Figure 7A:
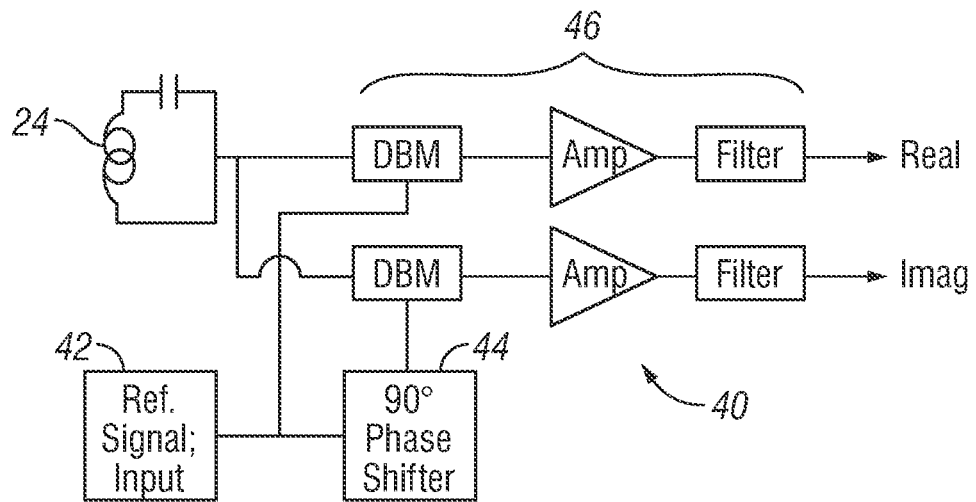
FIG. 7a is a schematic circuit diagram showing the interaction between the various components of the receiving circuit of the combined receiving and transmission coils.
Figure 7B:
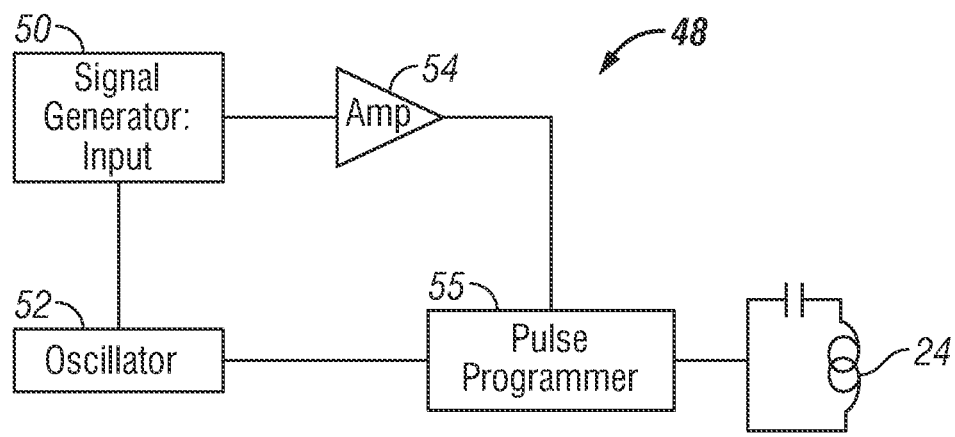
FIG. 7b is a schematic circuit diagram showing the interaction between the various components of the transmitting circuit of the combined receiving and transmission coils.

Referring to FIG. 7a, the receiver circuit 40 of the combined transmission and reception coils 24 comprises a reference signal input generator 42 and a 90° phase shifter 44 connected to a standard amplification and filtering system 46 in order to provide a real and imaginary output signal as a result of the signal received from the coil 24. Referring to FIG. 7b, the transmitter circuit 48 of the combined transmission and reception coils 24 comprises a signal generator input module 50 and an oscillator 52 which are linked to an amp 54 and a pulse programmer 56 in order to transmit the required radio frequency through coil 24. Though illustrated separately in FIGS. 7a and 7b, it will be understood that these circuits may be combined or integrated in order to provide the required transmission and reception capability of combined transmission and reception coils 24.

The secondary electromagnet housing 20 provides the magnetic gradient using coils Gx, Gy, and Gz which selectively (depending upon whether the electromagnet is on or off) provide a graduated magnetic field within the throughbore 36 of the apparatus in the x, y, and z directions respectively indicated by the reference axes R in FIG. 1. This arrangement provides the graduated magnetic field required by the flow rate calculation process described subsequently.

The profile of both the primary permanent magnet 16 and the secondary electromagnet 20 are arranged in the present embodiment, such that they can be housed within the outermost recess 18 and innermost recess 22 respectively in order to maintain a consistent diameter of throughbore 36 through the apparatus 10 such that disturbance of the fluid flowing from the pipe 14 through the apparatus 10 is minimized.

A second embodiment of the present invention having a number of modifications will now be described. Many components of the second embodiment are the same as those described in relation to the first embodiment. Such components will not be described any further. In addition, a number of components in the second embodiment correspond to similar components previously described in relation to the first embodiment, and where this applies, similar reference numerals will be used.

Referring to FIGS. 9 to 13, the apparatus 100 in accordance with the second embodiment of the present invention comprises an outer housing 120 surrounding a primary magnet 160. Primary magnet 160 has an inner ring 160A and an outer ring 160B. A secondary electromagnet is provided in housing 215 as discussed subsequently. Transmission/reception coil housing 205 is provided on the internal bore of the apparatus 100. The housing 205 may be made of a material such as Poly-Ether-Ether-Ketone (PEEK) or a nickel alloy such as Inconel®. The required pressure rating using (PEEK) is generally achieved using a housing 205 having a very thick wall (in the region of 20 mm). Such a wall generally degrades the magnetic field strength at the center of the flow path since magnet strength decreases with radial distance from the magnet. The thickness required using Inconel.RTM. is much less (in the region of 7 mm). In addition, the use of Inconel® (which has permeability comparable with free space ($\mu r \approx 1$)), concentrates the magnetic field into the flow path, thereby increasing the magnetic strength homogeneity.

The housing 205 in the present embodiment is provided with recessed tracks (not shown) which are machined onto the outer surface of the housing 205 during manufacture. Additional shapes may also be machined onto the outer surface in order to accommodate components such as the transmission and reception coil capacitors used in the transmission and reception circuit. Electrical insulation (not shown) such as adhesive insulant is also provided between the transmission/reception coil and the housing 205.

Figure 10:
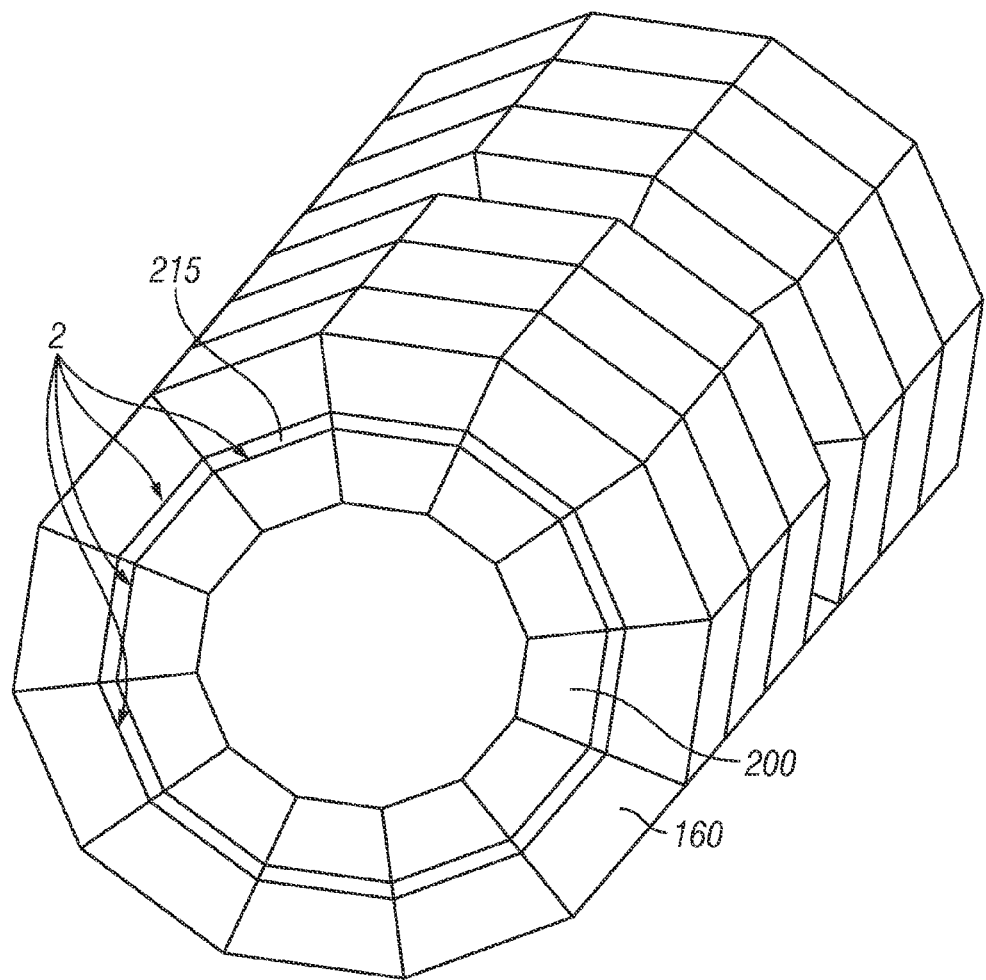
FIG. 10 is a schematic perspective view of the magnet configuration used in the apparatus of FIG. 9.
Figure 11:
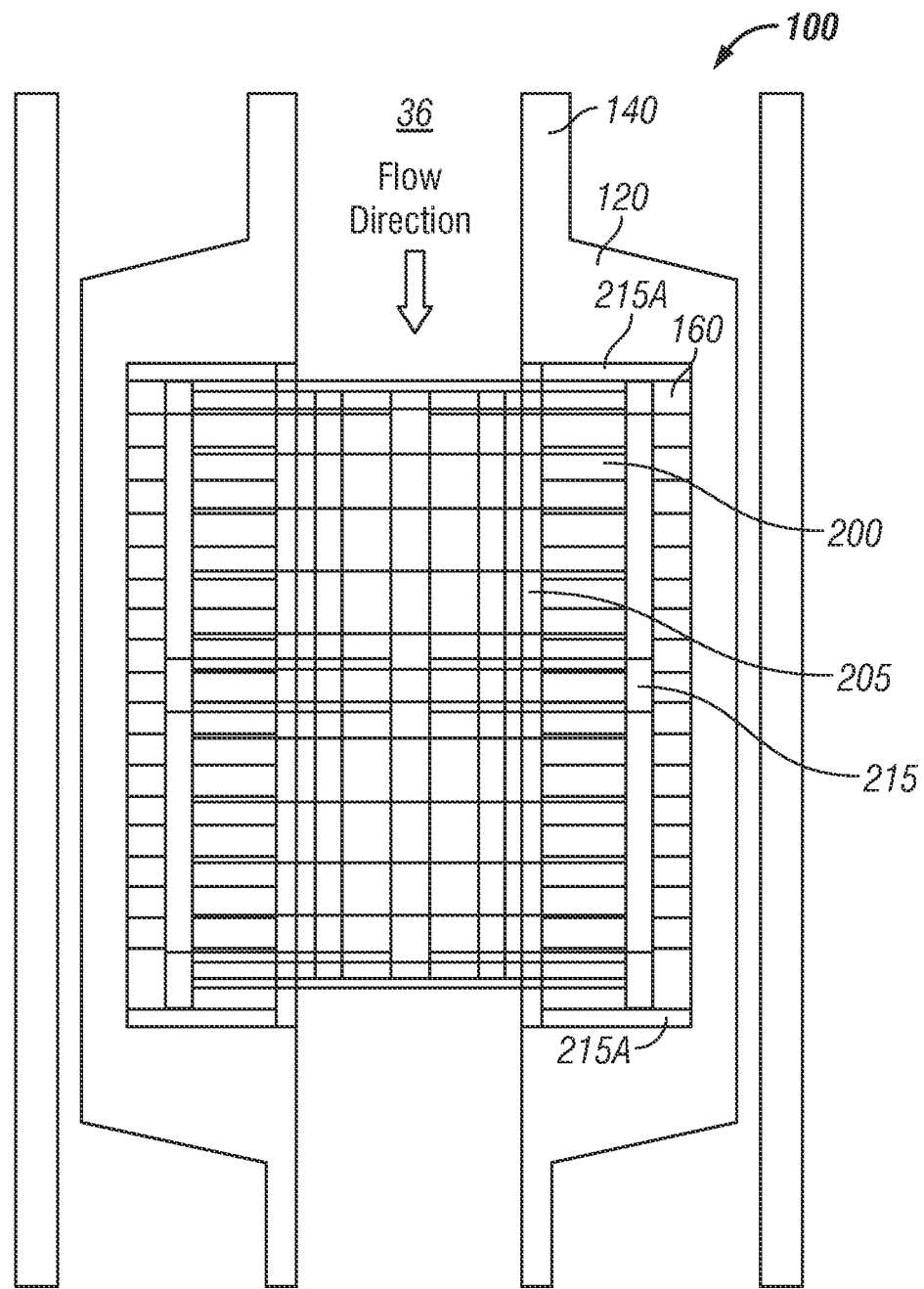
FIG. 11 is a transverse side view of the apparatus of FIG. 9 showing the gradient and transmission coils.

In further contrast, with the first embodiment, the apparatus 100 has gradient coils Gx, Gy, Gz mounted in tubing 215 between the primary magnet portions 160A and 160B. This separates the magnets 160A and 160B from one another which increases the combined efficiency of the magnets in producing a high strength homogeneous magnetic field in the flow path. The tubing 215 also provides mechanical support to retain the primary magnet and to provide support against the pressure exerted from the flow. In the present embodiment, the tubing 215 is made from high permeability iron and is dodecagonal in shape (as shown in FIG. 10). A pair of axial end members 215A are also provided in order to provide a magnetically permeable path for the magnetic field.

Figure 12:
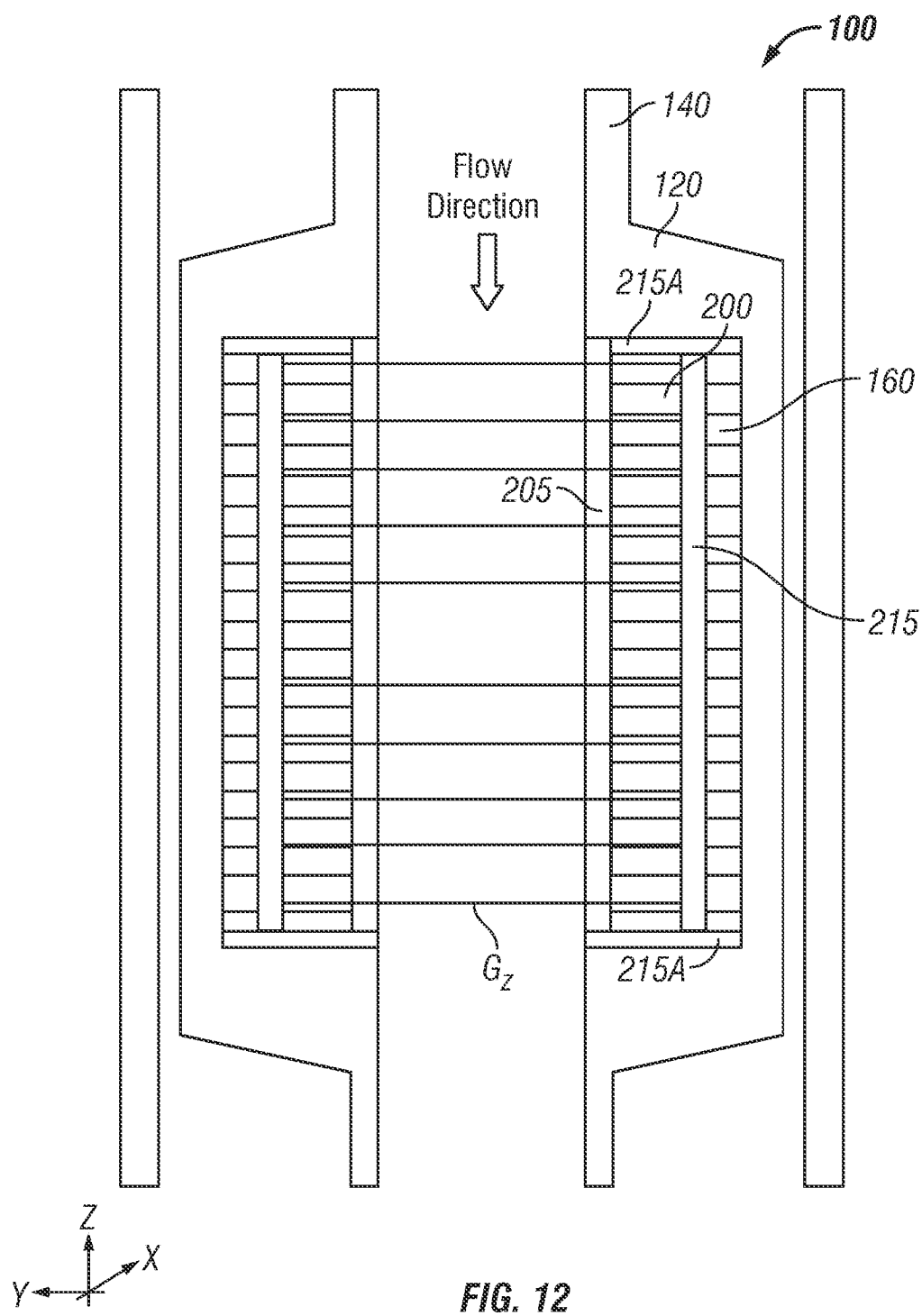
FIG. 12 is a schematic view of the component of the gradient coils of FIG. 10 which act in the z-axis direction.
Figure 13:
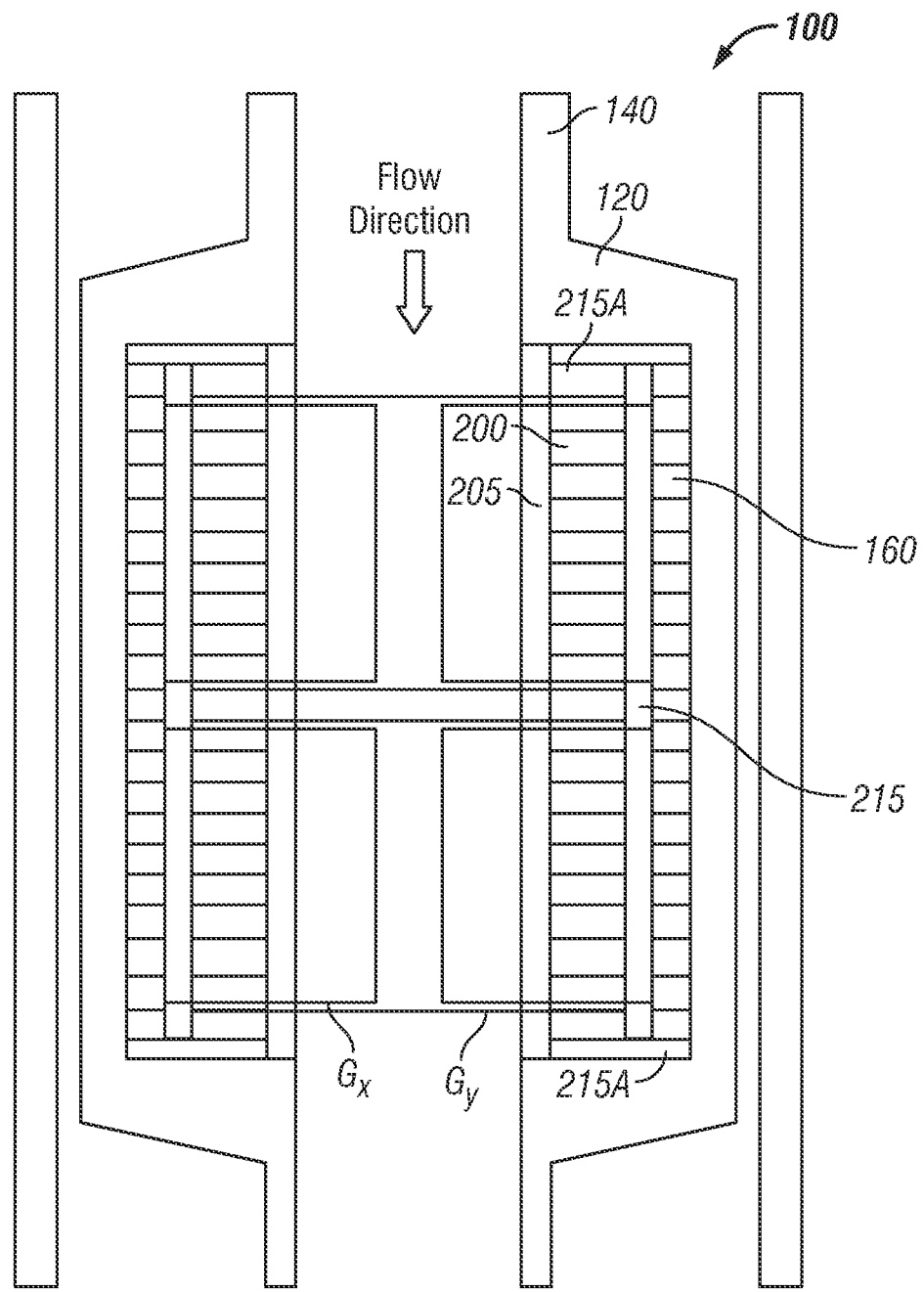
FIG. 13 is a schematic view of the component of the gradient coils of FIG. 10 which act in the x and y-axis directions.

As seen in FIG. 12, tubing 215 houses the axial gradient coil along the flow path (Gz) on the inner surface and the orthogonal gradients (Gx and Gy) on the outer surface (see FIG. 13). Again, these coils are provided in recessed tracks on the tubing 215 and are insulated from the tubing itself using adhesive insulant. The gradient coils are capable of imparting a variable magnetic field as discussed subsequently and in this regard can be considered as an electromagnet.

The tubing 215 is provided with a tubular inner diameter in order to provide minimal frictional losses to the fluid passing therethrough, and a dodecagonal outer surface which allows the tubing to fit within the rings of magnets.

In use, each embodiment of the apparatus 10 operates in an identical fashion by utilizing Nuclear Magnetic Resonance (NMR) techniques in order to determine the volume fraction of multiphase flow produced from a wellbore. In addition to determining the fraction of each phase present in the flow, the invention may also be used to determine the rate of fluid flowing from the wellbore. The embodiments described determine the phase fraction of fluid containing oil, gas and water phases; however, it will be understood by the skilled reader that further and/or different phases may be determined using the apparatus and method described.

For clarity the phase fraction analysis process will firstly be described followed by a description of the flow measurement process; however, both of these processes may be effectively carried out simultaneously by configuring the control system of the apparatus 10 to rapidly alternate between fraction analysis mode and flow measurement mode. This alternation between modes is typically performed at a rate of approximately one second for each mode i.e. the control system will allow the fraction analysis mode to operate for one second and then allow the flow measurement mode to operate for one second before switching back to the fraction analysis mode and so on as required. The skilled reader will note that this time may be altered to suit the specific situation.

The method of using the first embodiment of the apparatus will be described in the following description; however, the skilled reader will realize that either embodiment may be used.

In the embodiment shown, the apparatus 10 is installed in-line with a fluid flow pipe 14. As produced fluids flow into the apparatus 10, they enter the substantially homogeneous primary magnetic field generated by primary magnet 16. Atomic nuclei having a non-zero magnetic moment that are present in the fluids flowing through the apparatus 10 align themselves with the axis of the primary magnetic field. Fluids having a non-zero magnetic moment include $^1$H, $^{13}$C, $^{31}$P and $^{15}$N. In this embodiment (and in many NMR applications in general) $^1$H is the most commonly measured of these since it is naturally present in hydrocarbons such as those produced from wellbores. The nuclei of flow within the throughbore 36 of the apparatus 10 including water, oil and gas are now aligned with the direction of the primary magnetic field.

A radio frequency (RF) pulse signal is now transmitted into the throughbore 36 using the transmission circuit 48 of the combined transmission and reception coils 24. The frequency of the RF pulse will be transmitted at a frequency which is known to excite the atomic nucleus of $^1$H (typically in the region of between 40-45 MHz for a 1 Tesla static magnetic field such that it resonates at its natural resonant frequency (this is known as the Larmour frequency). This ensures that any $^1$H nuclei present in fluid flowing through the throughbore 26 will resonate in response to the RF pulse signal. The frequency (v) required to resonate the nuclei may be determined using the following equation:

$$v = \frac{\gamma B}{2\pi} \qquad \text{Eq. (1)}$$

where .gamma. is the gyromagnetic ratio of the nucleus and B is the magnetic field.

While resonating, the nuclei emits a radio signal at a frequency corresponding to its resonating frequency.

The frequency at which the nuclei present in the fluid flow resonate after having being excited by the RF pulse signal is detected by the receiver circuit 40 of the combined transmitter and reception coils 24. In a mixture of phases such as in the present embodiment, the resonance described provides molecular information such as the bond type and the environment surrounding the nuclei. From this, the ratio of the signal being received from the resonating nuclei to the background frequency of the RF pulse may be calculated. The skilled reader will understand that this value is known as Chemical Shift and is measured in parts per million ("ppm").

The chemical shift ($\delta$) recorded by the apparatus may now be used to determine the ratio of oil and gas (combined) to water using the following equation:

$$\delta = \frac{v_{sample} - v_{reference}}{v_{reference}} \times 10^6 \text{ ppm} \qquad \text{(Eq. (2))}$$

In this regard, the separation between the phases is increased by ensuring that good magnetic field homogeneity is provided by the primary permanent magnet 16 in order to produce a relaxation time graph peak with a small bandwidth.

However, as stated previously it is desirable to measure the ratio of oil to gas also in order to determine the ratios of oil, gas and water in the multiphase fluid, without assuming presence of other phases. In general, the chemical shift between oil and gas nuclei is too small to measure accurately by using the chemical shift method. Therefore, the present invention determines the ratio of oil to gas by comparing the $T_1$ relaxation times (described subsequently) of each hydrocarbon. This is possible since the $T_1$ relaxation times of gaseous hydrocarbons are longer compared to the $T_1$ relaxation times of liquid hydrocarbons.

In addition to causing the nuclei of each phase to resonate, the energy supplied by the RF pulse signal from the combined transmission and reception coil 24 causes the nuclei of each phase to be knocked off their previous alignment with the primary magnetic field. After the RF signal has been pulsed, the spins (nuclei which have been subjected to a magnetic field) will tend to relax back to their state of equilibrium in which they are re-aligned along the primary magnetic field. The time taken for the spins to relax back to their state of equilibrium after the RF signal has been pulsed off is known as the $T_1$ relaxation time of the nuclei.

It is possible to measure the $T_1$ relaxation times of the oil and gas using the apparatus 10 by monitoring the angle through which the nuclei of each phase of the flow is tilted with respect to the primary magnetic field at any given time (which must be less than the relaxation time) after the RF signal has been pulsed. This is done by measuring the time taken for the magnitude of the radio frequency received from the nuclei to reach a maximum value in the direction of the primary magnetic field and the time taken for a minimum value in the direction orthogonal to the primary magnetic field direction, which may be performed using the combined transmission and reception coils 24. This results in two distinct $T_1$ relaxation times being detectable; one for the oil phase and one for the gas phase. The proton density (PD) of each hydrocarbon phase is now calculated by integrating the area under each peak of the accumulated $T_1$ relaxation time density. The graph is derived by applying an inverse algorithm to the $T_1$ relaxation time measurement extracted using an inversion recovery sequence. Using the proton density measurement the volume fraction is now calculated using the following equation:

$$V = \frac{MW_s}{\rho_s} \times \frac{1}{Av} \times \frac{PD}{\alpha R_{1H}} \qquad \text{Eq. (3)}$$

where $MW_s$ is the molecular weight, $\rho_s$ is the density of the sample, Av is the Avogadro number, PD is the proton density, $\alpha$ is the natural abundance of $^1H$ and $R_{1H}$ is the number of $^1H$ for 1 molecule of the phase.

The sequence applied here is such that the required measurement time is less than the transit time ($\tau$) of the flow. The method of determining the proton density is performed using a 1-dimensional hydrogen nuclei (1D-1H) sequence in combination with an inversion recovery sequence for $T_1$ measurement and Carr-Purcell-Meiboom-Gill (CPMG) sequence for $T_2$ measurement.

However, the above merely returns values for the volume of the relevant phases and, as previously mentioned, not the phase fraction. In order to calculate the phase fraction, the following equation may be used:

$$\frac{V_1}{\sum_{i=1}^{n} V_i} = \frac{\frac{MW_1}{\rho_1} \times \frac{PD_1}{R_{1H1}}}{\sum_{i=1}^{n} \left(\frac{MW_i}{\rho_i} \cdot \frac{PD}{R_{1H1}}\right)} \qquad \text{Eq. (4)}$$

where n is the number of phases present in the sample.

It should be noted that in a sample containing just two phases (a and b), the equation can be simplified to:

$$\frac{V_a}{V_a + V_b} = \frac{1}{1 + \frac{MW_b \times \rho_a \times PD_b \times R_{1Ha}}{MW_a \times \rho_b \times PD_a \times R_{1Hb}}} \qquad \text{Eq. (5)}$$

Each of the fractions of oil, gas, and water have therefore been calculated using the apparatus 10 without (as in some previous systems) requiring to assume that once the ratios of two phases in the flow have been calculated the third makes up the rest of the fluid.

The method and apparatus for determining the flow rate of the fluid flow will now be described.

Now that the ratio of each phase has been calculated, the $T_1$ relaxation time of each phase is known. The embodiment shown is capable of employing two alternative methods of calculating the flow rate of each phase through the apparatus 10. The first method is based upon the Time of Flight (TOF) of the spins along the apparatus 10. In this method a pulse signal is applied in a 'slice' at a first location along the throughbore 36 of the apparatus 10 in order to tilt the nuclei at that location. A detection area is then monitored downstream from the location at which the pulse signal was applied. The resultant NMR signal received by the reception circuit 40 of the combined transmission and detection coils 24 will now be increased by every fully tilted spin entering the detection area and will be decreased with every fully tilted spin leaving the detection area. The overall net signal can therefore be related back to the flow of phase through the apparatus. This allows the velocity of the flow (v) to be calculated using the transit time ($\tau$) and the distance of the detection area (d) using the following equation:

$$\tau = \frac{d}{v}$$ Eq. (7)

The second alternative method of measuring the flow through the apparatus 10 uses the gradiated magnetic field provided by the secondary electromagnet 20. A gradient echo sequence is imparted on the flow such that the nuclei of the flow rotate about their axes. In a stationary flow this results in no net accumulation of phase signals since the nuclei experience the same balanced gradient with respect to time. However, in a dynamic flow the magnetic field experienced by the nuclei will change as the nuclei flow along the throughbore 36 of the apparatus 10 due to the magnetic field gradient provided by electromagnet 20. This variation of magnetic field, dependent upon the movement of the flow along the throughbore 36 of the apparatus 10, results in an accumulation of phase signal. This is dependent upon the velocity of the flow through the apparatus 10 and the strength and duration of the magnetic field gradient supplied by the electromagnet 20. The accumulation in phase ($\phi$) which may be directly correlated to the velocity of the flow is given by:

$$\phi = \gamma B_0 \int dt + \gamma \int n(t) G_n(t) dt$$ Eq. (8)

where $B_0$ is the magnetic field provided by the primary magnet, n represents the position of the spins within the throughbore in either the x, y, or z axes (as shown in FIG. 1) and $G_n$ is the magnitude of the magnetic field gradient being applied by the electromagnetic 20 in the n-axis direction.

The method described previously allows both the flow rate and proportion of each phase to be calculated using a single apparatus 10. Furthermore, the system and apparatus described does not require users of the apparatus to be safeguarded from levels of operational danger other than that normally expected in such oil and gas exploration operations. Specifically, the apparatus and method described does not require the user to be protected against e.g. radiation and biological hazards.

Figure 14:
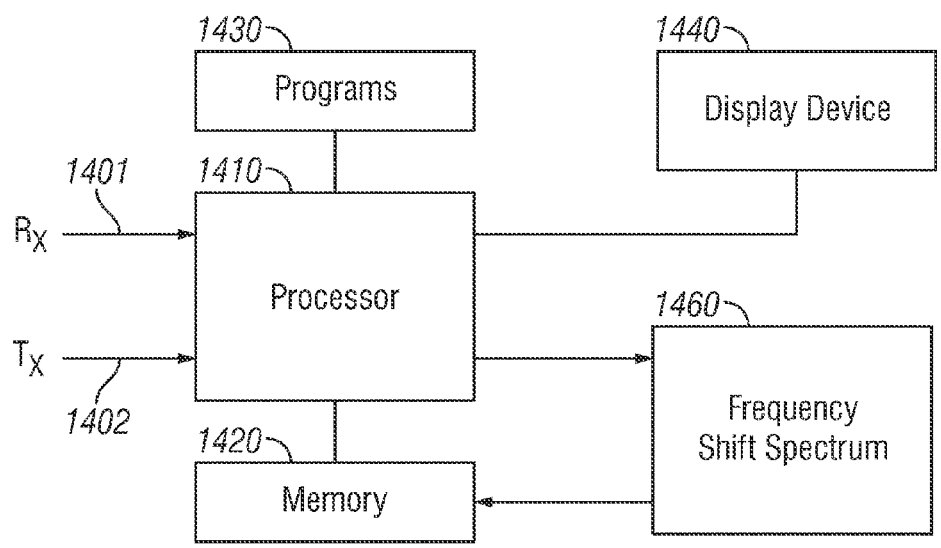
FIG. 14 is a functional diagram of a circuit for performing compositional analysis of hydrocarbons according to one embodiment of the disclosure.

In other aspects, compositional analysis of hydrocarbons produced from the wellbores may be provided using the imparted and detected radio frequency signals. FIG. 14 shows one embodiment of an apparatus that may be utilized for estimating species of hydrocarbons of downhole fluids. The apparatus of FIG. 14, in one aspect, may include a processor, such as a microprocessor or a computer 1410 and a data storage device 1420, which may be any suitable device, including, but not limited to, a solid state memory, compact disc, hard disc, and tape. One or more programs, models and other data (collectively referred to as "programs" and designated by numeral 1430) may be stored in the data storage device 1420 or another suitable device accessible to the processor 1410 for executing instructions contained in such programs. A display device 1440 may be provided for the processor 1410 to display information relating to the compositional analysis, as described in more detail below.

In one aspect, the processor 1410 may compute the frequency difference or frequency shift 1460 between the original imparted or perturbing signal 1402 and the detected signal 1401. This phenomenon is also known as the chemical shift. In one aspect, the processor 1410 may estimate or determine the composition (species of the produced hydrocarbons) using the frequency or chemical shift.

Figure 15:
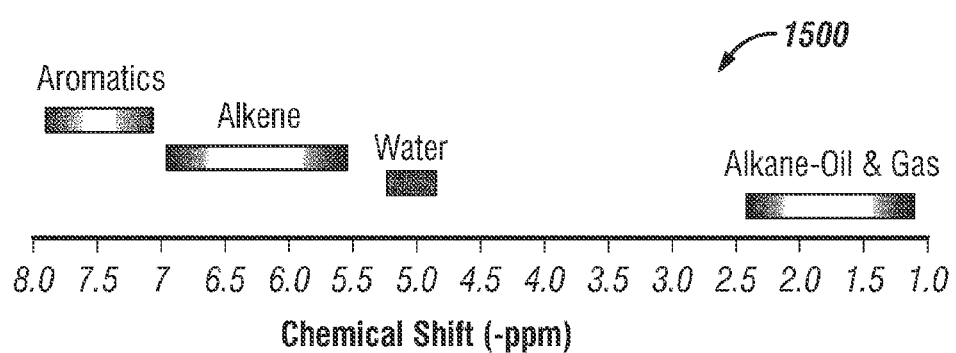
FIG. 15 is a visual representation of the relationship between certain species of a hydrocarbon and the frequency shift (also referred to as chemical shift) between an imparted radio frequency signal on a fluid and a detected radiofrequency signal from the fluid.

FIG. 15 shows a relationship 1500 of the frequency or chemical shift and various species of a hydrocarbon. For example, a chemical shift between −2 to −1.0 parts per million (ppm) indicates the presence of alkane, a chemical shift between −7 to −5.5 ppm indicates the presence of Alkene, and a chemical shift between −8.0 and −7.0 ppm indicates the presence of aromatic compounds. Aromatic compounds are the compounds that have a benzene ring structure, such as toluene, benzene and zylene. The data shown in FIG. 15 may be stored in the data storage device 1420 for use by the processor 1410.

Figure 16:
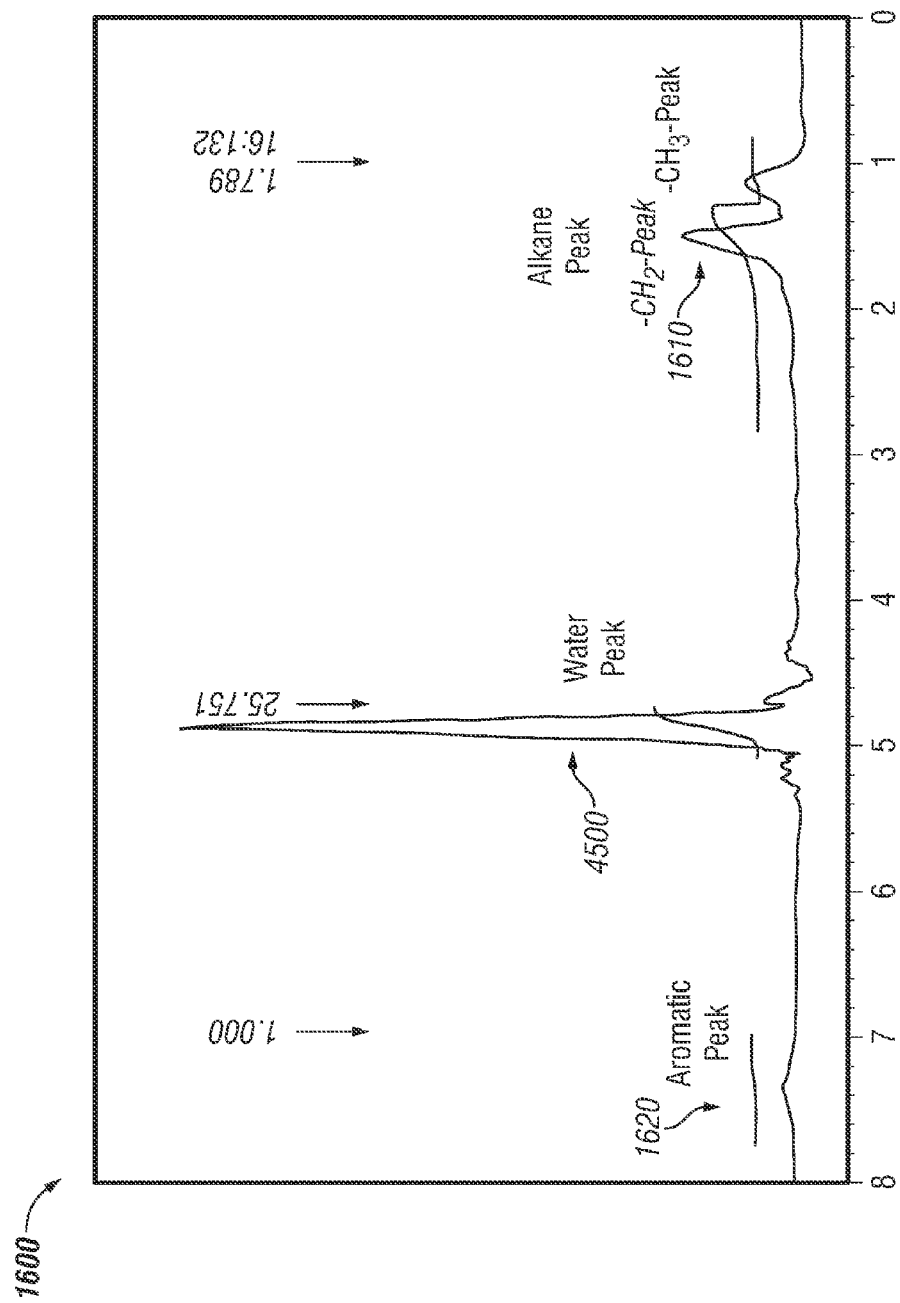
FIG. 16 is a frequency shift spectrum of certain species of a hydrocarbon.

FIG. 16 shows a chemical shift curve or spectrum 1600 relating to the various species of a hydrocarbon produced from the wellbores. In another aspect, the processor 1410 may estimate an amount of the species from the spectrum 1600. In one aspect, an area under the chemical shift curve 1600 may be integrated to estimate the amount of the species in the hydrocarbon. Therefore, the area under the curve section 1610 will provide the amount or fraction of alkane in the fluid sample, while the area under section 1620 will provide the amount or fraction of aromatics in the fluid sample. Composition of the species may therefore be estimated as a relative value or as an absolute value.

In another aspect, the programs 1430 may include instructions for the processor to determine the relaxation times and provide therefrom a detailed analysis of the species, such as a breakdown of the types of alkanes. Relaxation time, as described previously, is the time the signal emitted by the nuclei takes to decay. There is a direct relationship between the density of the alkane (which is linked to the length of the carbon chain) and the relaxation time. The higher the density of alkane, the longer the relaxation time.

In another aspect, the compositional analysis of hydrocarbon described herein may be utilized to provide information for a PVT analysis of the hydrocarbon. From the estimated composition of the hydrocarbon, as described above, the overall PVT properties of the hydrocarbon may be determined.

In prior art techniques, the PVT analysis of the hydrocarbon is typically done by taking a sample of the downhole fluid at a known pressure and temperature and various tests are conducted to determine the properties of the fluid, such as the bubble point and density and viscosity at various temperatures and pressures. The breakdown of the hydrocarbon to its core components is then made. The PVT properties of the core components are well known and may be reconstituted to provide an overall hydrocarbon PVT property. A known reconstitution technique is used. For example, for gas hydrocarbons, gas chromatography may be performed to break down the gas into its individual components and based on this composition, an overall gas property may be recalculated.

The technique of compositional analysis described herein bypasses taking a fluid sample and rigorous tests typically performed to determine the PVT properties of the hydrocarbon. Furthermore, in the present method, the measurements are done in real time (in-situ) as opposed to 'sampling' of the hydrocarbon.

The dimensions of the apparatus may be altered during the manufacturing stage dependent upon the particular downhole or subsea conditions in which it is to be used. In this regard, the space requirements of the components may be balanced based on the accuracy of desired measurement, which may be relevant for the primary magnet 16 and the electromagnet 20. Additionally, the apparatus described above may be used in a wellbore or in-line with any portion of the production tubing. Alternatively the apparatus may be used off site as an off-site measurement and analysis tool.

Figure 17:
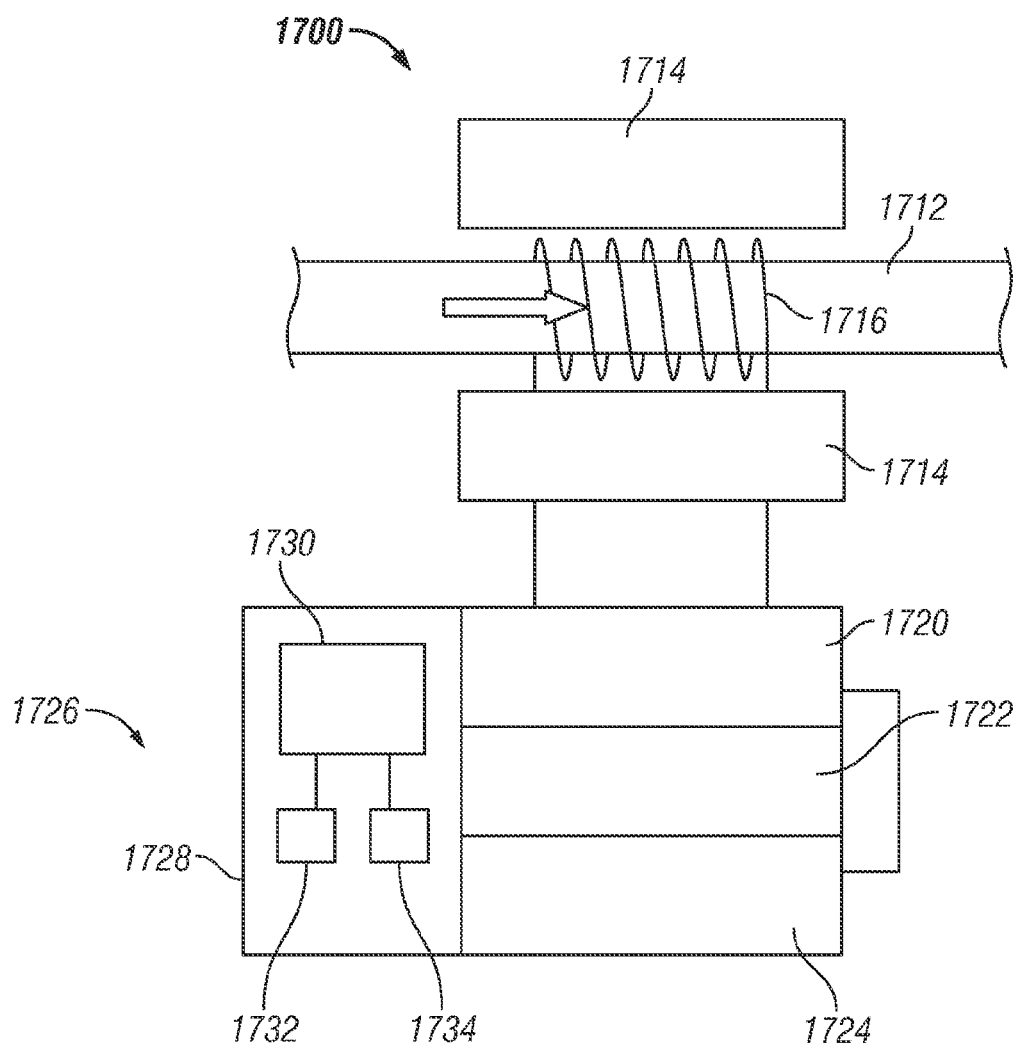
FIG. 17 shows an exemplary Nuclear Magnetic Resonance (NMR) flow meter device for estimating a volume of a fluid phase using the exemplary methods of the present disclosure.

In another aspect, the present disclosure provides a method of determining volumes of liquid and gas phases of a multiphase fluid. Phase volume is determined for a multiphase fluid in a constant measurement volume, such as in a volume of the NMR apparatus of FIG. 17. FIG. 17 shows an exemplary Nuclear Magnetic Resonance (NMR) flow meter device 1700 for estimating a volume of a fluid phase using the exemplary methods of the present disclosure. In one embodiment, the fluid is a multiphase fluid. In another embodiment, the fluid is a fluid flowing in a production system or a pipe for transportation of hydrocarbons. The exemplary NMR flow meter 1700 includes a section 1710 for providing NMR excitation pulses to the fluid and obtaining NMR signals in response to the NMR excitation pulses from the fluid, and a testing unit 1726 for receiving the NMR response signals from the detection section 1710 and performing calculations on the received NMR response signals to obtain a phase volume.

The device 1700 includes a magnet 1714 which may be exterior to the detection pipe section 1712 for providing a static magnetic field in a volume of the detection pipe section 1712, and a radio frequency (RF) coil 1716. As fluid passes through the static magnetic field of magnet 1714, nuclear spins of atoms and molecules within the fluid align along the direction of the static magnetic field. The RF coil 1716 encloses a volume within the detection pipe section and is arranged to provide one or more NMR excitation pulses to the fluid in the device and to detect one or more NMR response signals from the fluid. Testing unit 1726 includes various circuitry for obtaining one or more NMR response signals from the fluid and estimating a parameter of interest of the fluid from the obtained NMR response signals. In one embodiment, the exemplary testing unit 1726 is coupled to the RF coil 1716 via preamplifier 1720. The exemplary testing unit 1726 includes a transmitter 1724 for providing an NMR excitation pulse to the RF coil 1716 via preamplifier 1720. In one embodiment, the transmitter 1724 provides multiple NMR excitation pulse sequences, each NMR excitation pulse sequence tuned to a selected nuclear resonance frequency. The exemplary testing unit 1726 also includes a receiver 1722 for receiving NMR response signals detected at the RF coil 1716 via the preamplifier 1720. Testing unit 1726 also includes an NMR a control unit 1728 for estimating one or more parameters of the fluid from the received NMR response signals using exemplary methods of the present disclosure. In one embodiment, the control unit 1728 may include a processor 1730, one or more computer programs 1732 that are accessible to the processor 1730 for executing instructions contained in such programs to obtain one or more fluid-related parameters such as a fluid phase volume, viscosity, water cut, and an emulsion stability parameter, for example, and a storage device 1734, such as a solid-state memory, tape or hard disc for storing the one or more parameters obtained at the processor 1730.

NMR signal amplitude measurements in a constant volume measurement device can be used to determine a liquid phase fluid volume fraction vs. gas phase volume fraction. As shown with reference to FIG. 17, fluids flow into apparatus 1700 where they enter the substantially homogeneous primary magnetic field generated by primary magnet 1714. The nuclei of the produced fluids thereby polarize along the direction of the primary magnetic field. A radio frequency (RF) pulse signal is transmitted into the throughbore 1712 using the transmitter 1724 of the combined transmission and reception coils 1716. A signal amplitude for the nuclei present in the fluid flow after having being excited by the RF pulse signal is detected by the receiver 1722 of the combined transmitter and reception coils 1716.

NMR signal strength for a phase is a function of phase volume and hydrogen index for the phase. Hydrogen index is proportional to the proton density in the sensitive volume of the measurement device. The hydrogen index of methane $CH_4$, for example, is proportional to the gas density:

$$HI_g = A\rho_g \qquad \text{Eq. (9)}$$

with A=2.25. Gas density, in turn, is temperature and pressure dependent and can be determined by equation of state (EOS) correlations such as those described by Londono et al (SPE paper #75721 (2002)) and by Drumdruk et al "Calculation of z-factors for natural gases using equations of states" in J. of Canadian Petro., v. 14, pp. 24-26 (1975).

In order to determine liquid and gas phase volumes, a calibration signal is first obtained. The calibration signal is used to scale NMR signal strength or signal amplitude. In one aspect, calibration signal strength M is determined for a calibration signal using 100% water, such as distilled water (HI=1) flowing in the production tubular. A calibration constant can be obtained using c=M/V, where V is the sensitive volume and M is the strength of the calibration signal at a given temperature. The value of the calibration constant may be temperature-dependent and can therefore be determined either by using a theoretical prediction or by obtaining values for calibration constants at a plurality of temperatures and interpolating the values when necessary.

In a multiphase fluid having liquid and gas phases, NMR signal amplitude m is described by $$m = C(T)(V_{gas} \cdot HI_{gas} + V_{liquid} \cdot HI_{liquid}) \qquad \text{Eq. (10)}$$

where c(T) is the temperature-dependent calibration constant, $V_{gas}$ is the volume of a gas phase, $V_{liquid}$ is the volume of a liquid phase, $HI_{gas}$ is the hydrogen index of the gas phase and $HI_{liquid}$ is the hydrogen index of the liquid phase. Most formation water has a hydrogen index that is close to unity. Salinity of water can affect the hydrogen index, and the hydrogen index can be determined when salinity is known or estimated. The hydrogen index of liquid hydrocarbon is also substantially close to one.

When $H_{liquid}$ is 1 and $HI_{gas}$ is known for example from Eq. (9), then Eq. (10) can be solved for gas volume to obtain:

$$V_{gas} = \frac{1 - m/M}{1 - HI_{gas}} V \qquad \text{Eq. (11)}$$

An equation similar to Eq. (11) can be derived for when $H_{liquid}$ is a known value not equal to 1. Such an equation may be suitable for obtaining $V_{gas}$ in subsea or downhole locations.

In various aspects, phase volume may be obtained at a surface location, wherein pressure is substantially close to 1 atm. At this (low) pressure, $HI_{gas}$ is substantially close to zero and thus $1-HI_{gas}$ is substantially close to 1. For an equation more suitable to volume phase estimation, Eq. (10) can be obtained for low pressure environments by noting that $V_{gas} \cdot HI_{gas} \ll V_{liquid} \cdot HI_{liquid}$. If $V_{liquid}$ is substantially non-zero, then $m \approx c(T)(V_{liquid} \cdot HI_{liquid})$ and the resultant NMR signal represents primarily the liquid phase(s):

$$V_{liquid} \approx \frac{m}{M} V \cdot HI_{liquid} \qquad \text{Eq. (12)}$$

If $H_{liquid}=1$, then $$V_{liquid} = \frac{m}{M}V \qquad \text{Eq. (13)}$$

and $$V_{gas} = V - V_{liquid} \qquad \text{Eq. (14)}$$

Alternatively, $V_{liquid}$ and $V_{gas}$ can be estimated using a first order Taylor expansion of Eq. (10):

$$V_{gas} = \frac{1-m/M}{1-HI_{gas}}V \approx (1-m/M)(1+HI_{gas})V \qquad \text{Eq. (15)}$$

and $$V_{liquid} = V - V_{gas} \qquad \text{Eq. (16)}$$

Thus, liquid phase volume and gas phase volume can be determined for a multiphase fluid flowing in a production tubing. Additionally, volumetric flow rates of each phase may be obtained from the obtained phase volumes and flow velocities.

In another aspect, the present disclosure provides a method of determining a stability of an emulsion (i.e., multiphase fluid) flowing in a production tubing. Emulsion stability can vary from very tight emulsions characterized by small and closely distributed droplets to very loose emulsions characterized by large and widely distributed droplets. Emulsion stability can be characterized by an emulsion stability parameter, the value of which indicates the type of emulsion. For instance, an emulsion stability parameter of about 7.0 indicates a very tight emulsion and an emulsion stability parameter of about 3.0 indicates a very loose emulsion.

As discussed below, the emulsion stability parameter is related to viscosity and water cut of the emulsion. Viscosity measurements can be determined from relaxation times of NMR signals obtained from the emulsion. Relaxation times of the emulsion i.e. $T_1$ (spin-lattice relaxation constant) and $T_2$ (spin-spin relaxation constant), for example, can be measured using the exemplary apparatus of FIG. 17. An exemplary relation between $T_1$, $T_2$ and the viscosity of a fluid is given below:

$$\frac{1}{T_1} = \frac{1}{T_2} = \frac{40\pi M_2 a^3 \mu}{9kT} \qquad \text{Eq. (17)}$$

where $$M_2 = \frac{9}{20}\left(\frac{\varepsilon_0}{4\pi}\right)^2 \frac{h^2 \gamma^4}{r^6} \qquad \text{Eq. (18)}$$

wherein $\varepsilon_0$ is the magnetic permeability of free space, h is Planck's constant divided by $2\pi$, $\gamma$ is the gyromagnetic ratio for an H proton, r is a distance between nearest protons in a molecule, $\mu$ is the viscosity of the fluid, k is the Boltzmann constant, and T is the absolute temperature.

Figure 18:
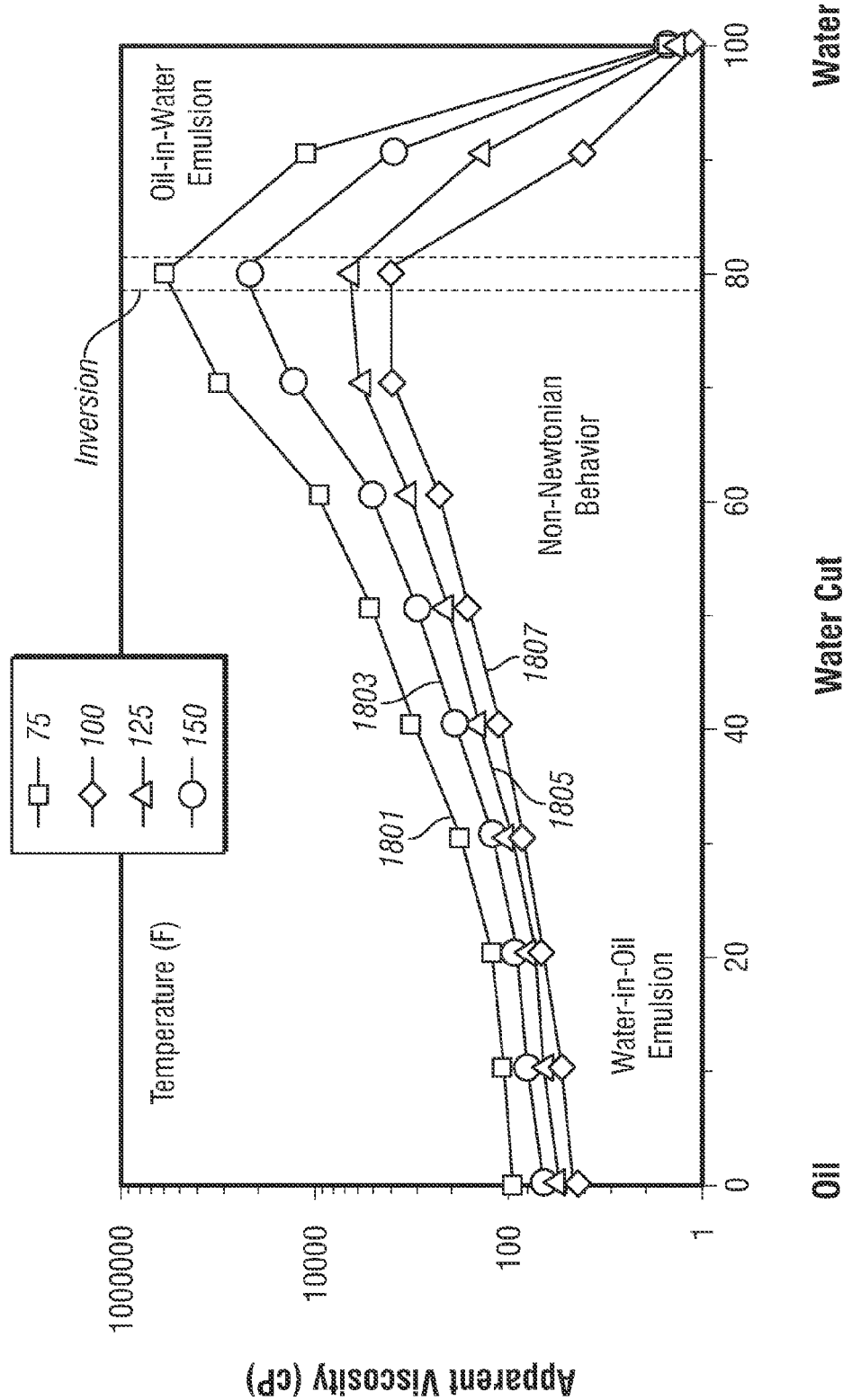
FIG. 18 shows an exemplary relation between emulsion viscosity and watercut or volume fraction of water in the emulsion.

FIG. 18 shows an exemplary relation between emulsion viscosity and watercut (WC) or volume fraction of water in the emulsion. Water cut can be determined using the exemplary methods disclosed herein or any other methods known in the art such as infrared measurements. In various emulsions, the viscosity of the emulsion is typically greater than the viscosity of either oil or water at a given temperature. For instance, FIG. 18 shows various curves of viscosity vs. water cut at different temperatures (75° F. (1801), 100° F. (1803), 125° F. (1805), 150° F. (1807)) for an emulsion of water and oil. At water cut of 0%, the emulsion is 100% oil and the emulsion has the viscosity of oil ($\mu_O$). At water cut of 100%, the emulsion is 100% water and the emulsion has the viscosity of water ($\mu_w$). As the water cut of the emulsion increases from 0%, the viscosity of the emulsion increases up to a water cut inversion point. In this region between 0% water cut and the inversion point, the emulsion is a water-in-oil emulsion. In the region between the inversion point and 100% water cut, the emulsion is an oil-in-water emulsion. The inversion point in exemplary FIG. 17 occurs at approximately a water cut of 80% water.

The viscosity of an emulsion depends on several factors: the viscosities of oil and water, the volume fraction of water (watercut), droplet size distribution, temperature, shear rate, amount of solids present, for example. The viscosity of the emulsion can be substantially higher than the viscosity of oil or water at a given temperature. The viscosity of an emulsion is related to the viscosity of the virgin crude oil at the same temperature by the following equation for $WC<WC_{inv}$:

$$\mu_L = \mu_0 e^{(5WC)}(1-3WC+\alpha(WC)^2) \qquad \text{Eq. (19)}$$

where $\alpha$ is the emulsification stability, $\mu_O$ is oil viscosity, $\mu_W$ is water viscosity, WC is the water cut and $WC_{inv}$ is the water cut inversion point. In addition, the following relation holds for $WC>WC_{inv}$:

$$\mu_L = \frac{\mu_w}{(WC)^{2.5}} \qquad \text{Eq. (20)}$$

Eq. (19) can be used to determine emulsion stability parameter $\alpha$ for an emulsion flowing in a production tubing. The method includes obtaining a relaxation time of an NMR signal of the emulsion, determining a viscosity of the emulsion from the obtained relaxation time, and determining emulsion stability using the determined viscosity and a value of water cut for the emulsion.

In various aspects, information of fluid emulsification assists production engineers in pipeline modeling by providing information on the drag exerted by the fluid. The present invention further provides an ability to image a flow pattern in the pipeline. This provides data for diagnosing plugs formations within the pipeline, thereby enhancing production pipeline and wellbore models. Knowing fluid composition also enables fluid analysis to obtaining fluid PVT properties.

The NMR measurement apparatus provides real-time measurement data which can be continuously updated. Updated compositional information can be fed back to a production model to improve flow analysis. Multiple technologies such as but not limited to infrared measurement (IR) can be used with the magnetic resonance measurements.

Therefore, in one aspect, the present disclosure provides a method of determining a volume of a phase of a multiphase fluid flowing in a tubular, including: imparting a magnetic field on the fluid to align nuclei of the multiphase fluid along a direction of the magnetic field; transmitting a radio frequency signal into the multiphase fluid to excite the nuclei; detecting a signal from the nuclei responsive to the transmitted radio frequency signal; determining an amplitude of the detected signal; and determining the volume of the phase flowing in the tubular using the determined amplitude and an amplitude of a calibration signal. When the phase is a liquid phase, the method further includes determining a relaxation time of the detected signal; and determining a viscosity of the multiphase fluid using the determined relaxation time. In one embodiment, the method includes determining a water cut of the liquid phase; and determining an emulsification stability parameter of the liquid phase from the determined viscosity and the determined water cut. Determining water cut of the liquid phase may include determining a proton density of the liquid phase from an accumulated relaxation time density. Also, the calibration signal may be obtained from a flow of water. Determining the volume of the phase may include determining a hydrogen index of a phase of the multiphase fluid. The method may further include determining a flow velocity of the phase; and determining a flow rate of the phase using the determined volume of the phase and the determined flow velocity of the phase. In various embodiments, the amplitude of the calibration signal is a temperature-corrected amplitude.

In another aspect, the present disclosure provides an apparatus for determining a volume of a phase of a multiphase fluid flowing in a tubular, the apparatus including a source configured to impart a primary magnetic field on the fluid to align nuclei of the multiphase fluid along a direction of the primary magnetic field; a source configured to transmit a radio frequency signal into the multiphase fluid to excite the nuclei; a detector for detecting a signal from the nuclei responsive to the transmitted radio frequency signal; and a processor configured to determine an amplitude of the detected signal and the volume of the phase flowing in the tubular using the determined amplitude of the detected signals and an amplitude of a calibration signal. The processor may be configured to determine a relaxation time of the detected signal; and determine a viscosity of the multiphase fluid using the determined relaxation time. In one embodiment, the processor is configured to determine a water cut of the liquid phase; and determine an emulsification stability parameter of the liquid phase from the determined viscosity and the determined water cut. The processor may be further configured to determine water cut of the liquid phase by determining a proton density of the liquid phase from an accumulated relaxation time density. The calibration signal may be obtained from a flow of water. The processor may be configured to determine the volume of the phase by determining a hydrogen index of a phase of the multiphase fluid. In various embodiment, the processor is configured to determine a flow velocity of the phase and determine a flow rate of the phase using the determined volume of the phase and the determined flow velocity of the phase. The amplitude of the calibration signal is typically a temperature-corrected amplitude.

In another aspect, the present disclosure provides a method of determining stability of an emulsion flowing in a production string, the method including imparting a primary magnetic field on the emulsion to align nuclei of the emulsion along a direction of the primary magnetic field; transmitting a radio frequency signal into the emulsion flowing in the production string; detecting a signal from the nuclei of the emulsion responsive to the transmitted radio frequency signal; determining an amplitude of the detected signal; determining a water cut of the emulsion using the obtained amplitude; determining a relaxation rate of a signal obtain from nuclei of the emulsion excited in response to the transmitted radio frequency signal; obtaining a viscosity of the emulsion from the determined relaxation time; and determining the stability of the emulsion from the determined emulsion viscosity and the water cut of the emulsion.

While the foregoing disclosure is directed to certain embodiments, various modifications will be apparent to those skilled in the art. It is intended that all such modifications fall within the scope and spirit of this disclosure and any claims that are or may be presented.

What is claimed is:

1. A method of determining an emulsion stability parameter of a multiphase fluid flowing in a tubular in order to determine a fluid flow rate, comprising:
   imparting a magnetic field on the multiphase fluid to align nuclei of the multiphase fluid along a direction of the magnetic field;
   transmitting a radio frequency signal into the multiphase fluid to excite the nuclei;
   detecting a signal from the nuclei responsive to the transmitted radio frequency signal;
   using a processor to:
   determine an amplitude of the detected signal;
   estimate a water cut of the multiphase fluid from the determined amplitude;
   determine a relaxation time of the detected signal;
   determine a viscosity of the multiphase fluid from the determined relaxation time of the detected signal;
   determine the emulsion stability parameter of the multiphase fluid from the determined viscosity, the estimated water cut and a curve that relates the viscosity, the water cut and the emulsion stability parameter;
   model the multiphase fluid with an emulsion characterized by the emulsion stability parameter;
   image a flow pattern of the multiphase fluid in the tubular using the emulsion model;
   determine a volume of the phase flowing in the tubular using the determined amplitude and an amplitude of a calibration signal; and
   determine the fluid flow rate from using one or more of the parameters determined above.

2. The method of claim 1, further comprising determining water cut of a liquid phase by determining a proton density of the liquid phase from an accumulated relaxation time density.

3. The method of claim 1, further comprising determining a volume of a phase of the multiphase fluid using an integrated signal from the calibration signal obtained from a flow of water and the amplitude of the detected signal.

4. The method of claim 3, wherein determining the volume of the phase further comprises determining a hydrogen index of a phase of the multiphase fluid.

5. The method of claim 3, further comprising:
   determining a flow velocity of the phase; and
   determining a flow rate of the phase using the determined volume of the phase and the determined flow velocity of the phase.

6. The method of claim 3, wherein the amplitude of the calibration signal is a temperature-corrected amplitude.

7. An apparatus for determining an emulsification stability parameter of a multiphase fluid flowing in a tubular in order to determine a fluid flow rate, comprising:
   a magnetic source configured to impart a magnetic field on the multiphase fluid to align nuclei of the multiphase fluid along a direction of the magnetic field;
   a source configured to transmit a radio frequency signal into the multiphase fluid to excite the nuclei;
   a detector for detecting a signal from the nuclei responsive to the transmitted radio frequency signal; and
   a processor configured to:
   determine an amplitude of the detected signal;
   estimate a water cut of the multiphase fluid from the determined amplitude;
   determine a relaxation time of the detected signal;

determine a viscosity of the multiphase fluid from the determined relaxation time;

determine the emulsification stability parameter of the multiphase fluid from the determined viscosity, the estimated water cut and a curve that relates the viscosity, the water cut and the emulsion stability parameter;

model the multiphase fluid with an emulsion characterized by the emulsion stability parameter;

image a flow pattern of the multiphase fluid in the tubular using the emulsion model;

determine a volume of the phase flowing in the tubular using the determined amplitude of the detected signals and an amplitude of a calibration signal; and determine the fluid flow rate from using one or more of the parameters determined above.

8. The apparatus of claim 7, wherein the processor is further configured to determine water cut of a liquid phase of the multiphase fluid by determining a proton density of the liquid phase from an accumulated relaxation time density.

9. The apparatus of claim 7, wherein the processor is further configured to determine a volume of a phase of the multiphase fluid using the calibration signal obtained from a flow of water and the amplitude of the detected signal.

10. The apparatus of claim 9, wherein the processor is further configured to determine the volume of the phase by determining a hydrogen index of a liquid phase of the multiphase fluid.

11. The apparatus of claim 9, wherein the processor is further configured to:

determine a flow velocity of the phase; and determine a flow rate of the phase using the determined volume of the phase and the determined flow velocity of the phase.

12. The apparatus of claim 9, wherein the amplitude of the calibration signal is a temperature-corrected amplitude.

13. A method of determining stability of an emulsion flowing in a production string in order to determine a fluid flow rate, comprising:

imparting a magnetic field on the emulsion to align nuclei of the emulsion along a direction of the magnetic field;

transmitting a radio frequency signal into the emulsion flowing in the production string;

detecting a signal from the nuclei of the emulsion responsive to the transmitted radio frequency signal;

using a processor to:

determine an amplitude of the detected signal;

estimate a water cut of the multiphase fluid from the determined amplitude;

determine a relaxation rate of the detected signal obtained from nuclei of the emulsion excited in response to the transmitted radio frequency signal;

determine a viscosity of the multiphase fluid using the volume determined from the determined relaxation rate;

determine an emulsion stability parameter of the emulsion from the determined emulsion viscosity, the water cut of the emulsion and a curve that relates the viscosity, the water cut and the emulsion stability parameter;

model the multiphase fluid with an emulsion characterized by the emulsion stability parameter;

image a flow pattern of the multiphase fluid in the tubular using the emulsion model;

determine a volume of the phase flowing in the tubular using the determined amplitude and an amplitude of a calibration signal; and determine the fluid flow rate from using one or more of the parameters determined above.

* * * * *